(12) United States Patent
Kaser et al.

(10) Patent No.: US 6,262,247 B1
(45) Date of Patent: Jul. 17, 2001

(54) POLYCYCLIC AROMATIC HYDROCARBON INDUCED MOLECULES

(75) Inventors: Matthew R. Kaser, Castro Valley; Yalda Azimzai, Hayward; Henry Yue, Sunnyvale, all of CA (US)

(73) Assignee: Incyte Genomics, Inc., Palo Alto, CA (US)

(*) Notice: Subject to any disclaimer, the term of this patent is extended or adjusted under 35 U.S.C. 154(b) by 0 days.

(21) Appl. No.: 09/386,493

(22) Filed: Aug. 30, 1999

(51) Int. Cl.[7] .......................... C07H 21/00; C12N 15/11; C12Q 1/68
(52) U.S. Cl. .................. 536/23.5; 536/23.1; 536/24.31; 435/6
(58) Field of Search ............................... 536/23.1, 23.5, 536/24.31; 514/44; 435/6

(56) References Cited

FOREIGN PATENT DOCUMENTS

WO 99/06439 * 2/1999 (WO).

OTHER PUBLICATIONS

Jaiswal et al., "Human dioxin–inducible cytochrome P1–450: complementary DNA and amino acid sequence", Science, 228:80–83, Apr. 1985.*

Sogawa et al., "Location of regulatory elements responsible for drug induction in the rat cytochrome P–450c gene", Proc. Natl. Acad. Sci. USA, 83:8044–8048, Nov. 1986.*

Kikuno et al., "Prediction of the coding sequences of unidentified human genes. XIV. The complete sequences of 100 new cDNA clones from brain which code for large proteins in vitro", DNA Research, 6:197–205, Jun. 1999.*

Hillier et al., "WashU–Merck EST Project", Genbank Accession No., AA478663, accessed by PTO, Jan. 27, 2000, Aug. 1997.*

NCI–CGAP, "National Cancer Institute, Cancer Genome Project (CGAP), Tumor Gene Index", Genbank Accession No. AA56554, accessed by PTO Jan. 27, 2000, Sep. 1997.*

Lamerdin, "Direct submission", Genbank Accession No., AD000684, accessed by PTO, Jan. 27, 2000, Apr. 1997.*

Hillier et al., "WashU–Merck EST Project", Genbank Accession No., R23086, accessed by PTO, Jan. 27, 2000, Apr. 1995.*

Lee et al., "Rat Genome Project: Generation of a Rat EST (REST) Catalog & Rat Gene Index", Genbank Accession No., AI010238, accessed by the PTO, Jan. 27, 2000, Jan. 1999.*

Marra et al., "WashU–HHMI Mouse EST Project", Genbank Accession No., AA244639, accessed by PTO, Jan. 27, 2000, Mar. 1997.*

Marra et al., "WashU–HHMI Mouse EST Project", Genbank Accession No., AA733664, accessed by PTO, Jan. 27, 2000, Jan. 1998.*

Lee et al., "Rat Genome Project: Generation of a Rat EST (REST) Catalog & Rat Gene Index", Genbank Accession No., AI010275, accessed by the PTO, Jan. 27, 2000, Jan. 1999.*

Marra et al., "WashU–HHMI Mouse EST Project", Genbank Accession No., AA002687, accessed by PTO, Jan. 27, 2000, Jul. 1996.*

Marra et al., "WashU–HHMI Mouse EST Project", Genbank Accession No., WO9392.1, accessed by PTO, Jan. 27, 2000, Oct. 1997.*

Lee et al., "Rat Genome Project: Generation of a Rat EST (REST) Catalog & Rat Gene Index", Genbank Accession No., AA945454, accessed by the PTO, Jan. 27, 2000, Jan. 1999.*

NCI–CGAP, "National Cancer Institute, Cancer Genome Project (CGAP), Tumor Gene Index", Genbank Accession No. AA613805.1, accessed by PTO Jan. 27, 2000, Oct. 1997.*

Stowers, S.J. and M.W. Anderson, "Formation and Persistence of Benzo(a)pyrene Metabolite–DNA Adducts", *Environmental Health Perspectives*, 62:31–39 (1985).

Bhat, R. et al., "ATP Depletion Affects the Phosphorylation State, Ligand Binding, and Nuclear Transport of the 4 S Polycyclic Aromatic Hydrocarbon–binding Protein in Rat Hepatoma Cells", *J. Biol. Chem.*, 271(51):32551–32556 (1996).

Bartsch, H. et al., "Impact of adduct determination on the assessment of cancer susceptibility", *Recent Results Cancer Res.*, 154:86–96 (1998).

Lamerdin, J.E., (Direct Submission), GenBank Sequence Database (Accession P81172), National Center for Biotechnology Information, National Library of Medicine, Bethesda, Maryland, 20894 (GI 3913818) Dec. 15, 1998.

* cited by examiner

Primary Examiner—Scott D. Priebe
Assistant Examiner—Peter Brunovskis
(74) Attorney, Agent, or Firm—Incyte Genomics, Inc.

(57) ABSTRACT

The invention provides novel nucleic acid molecules and encoded proteins associated with response to polycyclic aromatic hydrocarbon exposure. The invention also provides expression vectors, host cells, and antibodies. The invention also provides methods for screening or purifying ligands and diagnosing, treating or preventing disorders associated with polycyclic aromatic hydrocarbon exposure.

7 Claims, 11 Drawing Sheets

FIGURE 1A

```
5' CTTCA GTT CCT CGA AGA GAT TCA CTT TCA AAA ACA TCA ACT CCT TAT AAC AAA TCA
            11      20      29      38      47              56

AAC AAA GCA GCA AGC CAA CAA GGG ACC CCA TGG GAA ACA CTT GTC GTG TTT GCT
   65      74      83      92      101             110

ATC AAC TTG AAG CAA TTA AAC GTT CAA ATG AAT ATG AGT AAT GTA ATG GGA AAT
   119     128     137     146     155             164
                                    M   N   M   S   N   V   M   G   N

ACA ACT TGG ACA ACT AGT GGT TTG ACA ATG AGC ATG AAG AGC CAG ATG GGA AGT
   173     182     191     200     209             218
   T   T   W   T   T   S   G   L   T   M   S   M   K   S   Q   M   G   S

AAT CGT GAT CGA GAG ATC AGC ATG GGG GTT CTG GGA AGA TCA CAA TTA GAT
   227     236     245     254     263             272
   N   R   D   R   E   I   S   M   G   V   L   G   R   S   Q   L   D

TCT AAA GGA GGA GTA GTT GGA GGG ACC ATA GAT GTC AAT GCT TTG GAG ATG GTT
   281     290     299     308     317             326
   S   K   G   G   V   V   G   G   T   I   D   V   N   A   L   E   M   V

GCT CAT ATT TCT GAA CAT CCA AAT CAG CAA CCC AGT CAC AAA ATT CAG ATT ACT
   335     344     353     362     371             380
   A   H   I   S   E   H   P   N   Q   Q   P   S   H   K   I   Q   I   T

ATG GGT TCT ACT GAA GCT CGT GTT GAT TAC ATG GGC TCA AGT ATC CTC ATG GGC
   389     398     407     416     425             434
   M   G   S   T   E   A   R   V   D   Y   M   G   S   S   I   L   M   G
```

```
                 443             452             461             470             479             488
ATC TTC AGT AAT GCT GAT CTT AAG CAG GAT GAA TGG AAA GTA AAC TTG TAT
 I   F   S   N   A   D   L   K   Q   D   E   W   K   V   N   L   Y 497             506             515             524             533             542
AAT ACA TTG GAT TCA AGC ATA ACT GAT AAA AGT GAG ATT TTC GTC CAT GGA GAT
 N   T   L   D   S   S   I   T   D   K   S   E   I   F   V   H   G   D 551             560             569             578             587             596
TTG AAG TGG GAT ATT TTC CAA GTA ATG ATA TCA AGG TCA ACC ACA CCA GAT CTG
 L   K   W   D   I   F   Q   V   M   I   S   R   S   T   T   P   D   L 605             614             623             632             641             650
ATA AAA ATA GGA ATG AAG CTC CAG GAA TTT TTC ACA CAA CAA TTT GAT ACC AGC
 I   K   I   G   M   K   L   Q   E   F   F   T   Q   Q   F   D   T   S 659             668             677             686             695             704
AAA CGA GCT CTG TCT ACC TGG GGA CCA GTT CCT TAC CTT CCG CCA AAG ACA ATG
 K   R   A   L   S   T   W   G   P   V   P   Y   L   P   P   K   T   M 713             722             731             740             749             758
ACT AGC AAC CTA GAA AAA AGT TCA CAA CAA GAA CTT TTA CTT GAT GCA GCA CAT CAT
 T   S   N   L   E   K   S   S   Q   Q   E   L   L   L   D   A   A   H   H 767             776             785             794             803             812
AAT CGA TGG CCT GGA GTA TTG AAG GTG GTA TCA GGA TGC CAC ATA TCC TTA TTT
     W   P   G   V   L   K   V   V   S   G   C   H   I   S   L   F 821             830             839             848             857             866
CAG ATT CCA TTA CCA GAA GAT GGA ATG CAA TTT GGA TCA ATG AGC TTA CAT
 Q   I   P   L   P   E   D   G   M   Q   F   G   S   M   S   L   H
```

FIGURE 1B

```
      875        884        893        902        911        920
GGA AAT CAT ATG ACA CTG GCA TGT TTT CAT GGT CCA AAT TTT CGT TCA AAA TCT
 G   N   H   M   T   L   A   C   F   H   G   P   N   F   R   S   K   S 929        938        947        956        965        974
TGG GCC CTT TTT CAT TTA GAA GAA CCA AAT ATT GCT TTT TGG ACT GAA GCT CAG
 W   A   L   F   H   L   E   E   P   N   I   A   F   W   T   E   A   Q 983        992       1001       1010       1019       1028
AAA ATC TGG GAA GAT GGC TCC AGT GAT CAT AAT ATT ACA TAT GTA CAA ACA CTA
 K   I   W   E   D   G   S   S   D   H   N   I   T   Y   V   Q   T   L 1037       1046       1055       1064       1073       1082
GAT TTT CAC CTG GGT CAT AAT ACT ATG GTT ACC AAA CCA TGT GGT GCT TTG GAA
 D   F   H   L   G   H   N   T   M   V   T   K   P   C   G   A   L   E 1091       1100       1109       1118       1127       1136
AGT CCT ATG GCA ACA ATA ACC AAG ATA ACA AGG CGT CGC CAT GAA AAT CCA CCC
 S   P   M   A   T   I   T   K   I   T   R   R   R   H   E   N   P   P 1145       1154       1163       1172       1181       1190
CAT GGA GTA GCA AGT GTG AAA GAA TGG TTC AAT TAT GTT ACA GCT ACA AGG AAT
 H   G   V   A   S   V   K   E   W   F   N   Y   V   T   A   T   R   N 1199       1208       1217       1226       1235       1244
GAA GAG CTA AAT CTG CTT CGT AAT GTT GAT GCT AAC AAC ACT GAG AAT AGC ACT
 E   E   L   N   L   L   R   N   V   D   A   N   N   T   E   N   S   T 1253       1262       1271       1280       1289       1298
ACT GTG AAG AAT TCT AGT TTG TTG AGT GGA TTC AGA GGA GGT TCT AGC TAC AAC
 T   V   K   N   S   S   L   L   S   G   F   R   G   G   S   S   Y   N
```

FIGURE 1C

```
1307                1316        1325        1334        1343        1352
CAT GAA ACA GAG ACT ATC TTT GCA TTA CCA AGG ATG CAG CTT GAC TTT AAA TCC
 H   E   T   E   T   I   F   A   L   P   R   M   Q   L   D   F   K   S
1361                1370        1379        1388        1397        1406
ATT CAT GTT CAA GAA CCA CAG GAG CCT TCA TTA CAG GAT GCC AGC CTG AAG CCA
 I   H   V   Q   E   P   Q   E   P   S   L   Q   D   A   S   L   K   P
1415                1424        1433        1442        1451        1460
AAA GTA GAA TGT AGT GTG GTG ACA GAG TTC ACT GAC CAC ATT TGT GTG ACT ATG
 K   V   E   C   S   V   V   T   E   F   T   D   H   I   C   V   T   M
1469                1478        1487        1496        1505        1514
GAT GCT GAG CTC ATC ATG TTT CTT CAT GAT TTA GTA TCA GCT TAT CTT AAA GAA
 D   A   E   L   I   M   F   L   H   D   L   V   S   A   Y   L   K   E
1523                1532        1541        1550        1559        1568
AAA GAA AAA GCC ATC TTT CCA CCT CGG ATT TTA TCT ACT CGA CCA GGA CAA AAA
 K   E   K   A   I   F   P   P   R   I   L   S   T   R   P   G   Q   K
1577                1586        1595        1604        1613        1622
AGT CCA ATT ATT ATA CAT GAC GAC AAT TCC TCT GAT AAA GAT AGA GAA GAT AGC
 S   P   I   I   I   H   D   D   N   S   S   D   K   D   R   E   D   S
1631                1640        1649        1658        1667        1676
ATC ACT TAT ACT ACT GTG GAC TGG AGA GAT TTT ATG TGC AAT ACA TGG CAC CTA
 I   T   Y   T   T   V   D   W   R   D   F   M   C   N   T   W   H   L
```

FIGURE 1D

```
       1685            1694           1703           1712           1721           1730
GAA CCT ACT CTT AGA TTA ATT TCT TGG ACT GGA AGA AAG ATT GAT CCA GTA GGT
 E   P   T   L   R   L   I   S   W   T   G   R   K   I   D   P   V   G 1739            1748           1757           1766           1775           1784
GTT GAT TAT ATT CTT CAA AAA TTG GGC TTT CAT CAT GCT AGG ACT ACT ATT CCT
 V   D   Y   I   L   Q   K   L   G   F   H   H   A   R   T   T   I   P 1793            1802           1811           1820           1829           1838
AAA TGG CTT CAA AGA GGA GTC ATG GAT CCA CTG GAC AAG GTT CTG TCA GTT CTT
 K   W   L   Q   R   G   V   M   D   P   L   D   K   V   L   S   V   L 1847            1856           1865           1874           1883           1892
ATC AAA AAG CTC GGT ACT GCA CTA CAG GAT GAA AAG GAA AAG AAA GGC AAA GAC
 I   K   K   L   G   T   A   L   Q   D   E   K   E   K   K   G   K   D 1901            1910           1919           1928           1937           1946
AAA GAA GAA CAC TAA AAA AGT AAT TTG ATC TGT GAA CAA ATT ATG ATT GTG TCT
 K   E   E   H   *

1955            1964           1973           1982           1991           2000
GTT TTA CAC TGG AGT GTT TTT TTA GTA TAA TTT GAA ATA TAA CTT TAA 2009            2018           2027           2036           2045           2054
AAT AAT TCT AAA TTT GTG GCT ATA ATT AAA AGT TTG TAA GTT AAC CTG TTC TAG
```

FIGURE 1E

```
            2063        2072        2081        2090        2099        2108
     TTC CAT CAT TCT GTG TAC AGT GAA GTA TTG CAT GAT AAT GTA AAT TTT GTG AAA 2117        2126        2135        2144        2153        2162
     AAC TAG ATT AAA ATA TAT AAC TGC TTG TTA TGG TTT ATA ATT ATA TAA TGT GCA 2171        2180        2189        2198        2207        2216
     ATA CAA TTC CTG CAT CTT TAA AAT GTC TGC AGA ATA ACT GTG AAT TTT TTT GTT 2225        2234        2243        2252        2261        2270
     ATT GGA TTG GCC GTA ACT TTT AGA AAA AAA TCT TGT TGA TAA TGT GAT TTT 2279        2288        2297        2306        2315        2324
     GGG GAG GTC ATT AAT TGC TTT TTC TTT AAA TGT AGA CTT ATA TAA ATA CCT 2333        2342        2351        2360        2369        2378
     GTT TGT ATA TAG CTT GAG TAA TTG TGA TAT GAT TGT ATA CCA CTA AAA TAT TGT 2387        2396        2405        2414        2423        2432
     TAA CTA TTA TAA TAA AGT CAC AGT AAT GGT TTA AAA AAG AAA AAA GAA AAA AAA

AAA AAA A 3'
```

FIGURE 1F

```
                11              20              29              38              47              56
5' GCTTG AAG    GCG GGA AAA    TAC GGA ATG    GAG CGA CAG    GGA GTG GAC    CCC CAT GTG
         K       A   G   K      Y   G   M      E   R   Q      G   V   D      P   H   V 65              74              83              92             101             110
   AAA TGC AAA    GAC CAG GAA    CCG CAG CCC    TTG GGG GAG    AGC AAG GAG    CAT CCG CGG
    K   C   K      D   Q   E      P   Q   P      L   G   E      S   K   E      H   P   R 119             128             137             146             155             164
   AAC GAG GAG    GAA TGC GCT    GGT GGA CCA    GCT AGT AGT    GCC CAT CCG    TGC
    N   E   E      E   C   A      G   G   P      A   S   S      A   H   P      C 173             182             191             200             209             218
   TGG GAA GAG    AAC TGC GCT    GGT GGA CTC    TCG GAA GGG    TAC TTC TCC    CTG GAC TCA
    W   E   E      N   C   A      G   G   L      S   E   G      Y   F   S      L   D   S 227             236             245             254             263             272
   CAG CTG ACG    GTC CTG CTG    AAG GGG AAG    GCC CAG GAG    CTG ATC GAA    AAC ATC AAC
    Q   L   T      V   L   L      K   G   K      A   Q   E      L   I   E      N   I   N 281             290             299             308             317             326
   AGC ATT GAC    ATC CTG CAG    AAG AGA GCC    ATG ACC AAC    TTC AGG AAC    AGC CTG ACC
    S   I   D      I   L   Q      K   R   A      M   T   N      F   R   N      S   L   T 281             290             299             308             317             326
   AGC CGG CAA    AAG GAC CAT    GCA CTC ATG    ACC AAC TTC    AGG AAC AGC    CTG AAG ACC
    S   R   Q      K   D   H      A   L   M      T   N   F      R   N   S      L   K   T
```

FIGURE 2A

```
        335             344             353             362             371             380
AAG GTT TCG GAT CTG ACA GAG AAA TTA GAG GAG AGG ATC TAT CAG ATT TAT AAT
 K   V   S   D   L   T   E   K   L   E   E   R   I   Y   Q   I   Y   N 389             398             407             416             425             434
GAC CAC AAC AAG ATC CAG GAA AAG CTC CAA GAG TTC ACC CAG AAA ATG GCA
 D   H   N   K   I   Q   E   K   L   Q   E   F   T   Q   K   M   A 443             452             461             470             479             488
AAG ATC AGC CAT TTG GAG ACA GAG CTC AAA CAA GTC TGC CAC AGC GTG GAG ACT
 K   I   S   H   L   E   T   E   L   K   Q   V   C   H   S   V   E   T 497             506             515             524             533             542
AAA GAC CTG TGT CTC CAG CCT GAG CAG AGC CTA AGA CTC AGA TGG GGG
 K   D   L   C   L   Q   P   E   Q   S   L   R   L   R   W   G 551             560             569             578             587             596
GTG TAC CAC TCT AGG GGA AAG TCC CCA CCA CGT CCC GGC AAC TCA CAG CCC CCA
 V   Y   H   S   R   G   K   S   P   P   R   P   G   N   S   Q   P   P 605             614             623             632             641             650
CCA GAC GTG TTC GTT TCT GTG GCT GAA ACT ACT TCT CAG GCC ACT GCT TCA GAA
 P   D   V   F   V   S   V   A   E   T   T   S   Q   A   T   A   S   E
```

FIGURE 2B

```
         659         668         677         686         695         704
GTA CAG ACC AAC AGA GAT GGT GAA TGC TGA CAG CTG CCG GGA GAC TCA CGC CTT
 V   Q   T   N   R   D   G   E   C 713         722         731         740         749         758
AGT GAC AGT CTC CAG GAG AAG ACT GTG AGG CCA CCA TTT GGG CCA CAC TGA GAA 767         776         785         794         803         812
ATT GTT TTT CAT GGT TCT ATA ATG CAT CTT GGC AGA AAA CAA AAA CCC AAA 821         830         839         848         857         866
GCT CCT TGT GCT GAA CTC CCA AAA TGT AGC AAG TCC AGC CCT CTC CAT AGG CCC 875         884         893         902         911         920
AGG CTT CGT GCT CCC CAC CCT TGG CAA GTT CTC CCC ACC CCC AGC CCC ACA GTT 929         938
TAT TAA ATG TTT GAT TTT CAA AAA  3'
```

FIGURE 2C

```
                        9              18             27             36             45         54
5' CTC AAG ACC CAG CAG CAG TGG GAC AGC CAG ACA GAC ACG ATG GCA CTG AGC TCC
   L   K   T   Q   Q   Q   W   D   S   Q   T   D   T   M   A   L   S   S 63             72             81             90             99        108
   CAG ATC TGG GCC GCT TGC CTC CTG CTC CTC CTC GCC AGC CTG ACC AGT
   Q   I   W   A   A   C   L   L   L   L   L   A   S   L   T   S 117            126            135            144            153        162
   GGC TCT GTT TTC CCA CAA CAG ACG GGA CAA CTT GCA GAG CTG CAA CCC CAG GAC
   G   S   V   F   P   Q   Q   T   G   Q   L   A   E   L   Q   P   Q   D 171            180            189            198            207        216
   AGA GCT GGA GCC AGG AGC TGG AGC ATG CCC ATG TTC CAG AGG AGG CGA
   R   A   G   A   R   S   W   S   M   P   M   F   Q   R   R   R 225            234            243            252            261        270
   GAC ACC CAC TTC CCC ATC TGC ATT TTC TGC TGC GGC TGT TGT CAT CGA TCA AAG
   D   T   H   F   P   I   C   I   F   C   C   G   C   C   H   R   S   K 279            288            297            306            315        324
   TGT GGG ATG TGC TGC AAG ACG TAG AAC CTA CCT GCC CTG CCC TCC CCT CCC
   C   G   M   C   C   K   T         N   L   P   A   L   P   S   P   P 333            342            351            360            369        378
   TTC CTT ATT TAT TCC TGC TGC CCC AGA ACA TAG GTC TTG GAA TAA AAT GGC TGG 387                           396
   TTC TTT TGT TTT CCA AAA AAA AAA AAA AA 3'
```

POLYCYCLIC AROMATIC HYDROCARBON INDUCED MOLECULES

FIELD OF THE INVENTION

The present invention relates to nucleic acid molecules comprising at least fragments of human genes homologous to rat genes expressed in response to treatment with the polycyclic aromatic hydrocarbon benzo(a)pyrene. The invention also relates to the use of these molecules in diagnosis, prognosis, prevention, and treatment of human disorders such as cancer and its complications. The invention further relates to the use of these molecules in rat model systems for evaluation of therapies for disorders such as cancer and its complications.

BACKGROUND OF THE INVENTION

Phylogenetic relationships among organisms have been demonstrated many times, and studies from a diversity of prokaryotic and eukaryotic organisms suggest a more or less gradual evolution of biochemical and physiological mechanisms and metabolic pathways. Despite different evolutionary pressures, proteins that regulate the cell cycle in yeast, nematode, fly, rat, and man have common chemical or structural features and modulate the same general cellular activity. Comparisons of human gene sequences with those from other organisms where the structure and/or function may be known allow researchers to draw analogies and to develop model systems for testing hypotheses. These model systems are of great importance in developing and testing diagnostic and therapeutic agents for human conditions, diseases and disorders.

Polycyclic aromatic hydrocarbons (PAH), such as benzo(a)pyrene (BP), are ubiquitous environmental pollutants known to cause cancer in laboratory animals. PAH induce tumors in various tissues of animal species regardless of the route of administration. Human exposure to PAH in food, air, and water is increasing, and epidemiological studies show a higher incidence of lung, skin, and bladder cancer in individuals exposed to high levels of PAH, e.g. cigarette smokers and coke oven workers.

PAH are lipophilic compounds oxidatively metabolized to epoxides, quinones, and phenols by the body's cytochrome P-450-dependent monooxygenase and epoxide hydrase. These metabolites are conjugated to more hydrophilic metabolites, most of which are secreted. However, some of the metabolites are capable of binding extensively and covalently to cellular macromolecules, such as DNA. Formation of PAH-DNA adducts appears to be an essential first step in PAH-induced neoplasia. If the cell cannot repair the damaged DNA before synthesis occurs, then replication on the damaged template can result in mutation. The two most common reactive metabolites of BP which bind to DNA are diol epoxide derivatives formed by the sequential action of the cytochrome P-450-dependent monooxygenase system and epoxide hydrase. Other PAH, such as benzanthracene, chrysene, 3-methylcholanthrene, and dimethylbenzanthracene, are also converted to very reactive diol epoxides that bind to DNA in vivo. All of these diol epoxides have a similar structure involving an epoxide ring in the bay region and have been called "bay region diol-epoxides" (Stowers and Anderson (1985) Environ. Health Perspect. 62:31–39).

The major DNA adduct formed by BP metabolites is(+)-7β, 8α-dihydroxy-9α,10 α-epoxy-7,8,9,10-tetrahydrobenzo(a)pyrene (BPDEI) bound to the N2 of guanine residues. Similar adduct patterns are seen in each tissue examined in mice and rabbits regardless of dose, route of administration, or time of sacrifice after dose. Differences in tissue susceptibility to PAH-induced neoplasia between different tissues may be due to the method of adduct repair. The liver, which is relatively resistant to carcinogenesis by BP, removes DNA adducts by excision repair. Lung, skin, and brain, which are more susceptible to BP-induced carcinogenesis, have little excision repair and remove DNA adducts primarily by cell turnover. If turnover rates in tissues are slow, significant levels of PAH metabolite-DNA adduct can accumulate, especially if there is continuous long-term exposure to PAH. The persistence and accumulation of DNA adducts could inhibit replication and transcription and lead to mutagenesis and carcinogenesis (Stowers and Anderson, supra).

There is growing evidence that predisposition to cancer may reside in polymorphic genes involved in carcinogen metabolism and repair. One major goal of epidemiologists is the identification of individuals who are exposed to high levels of carcinogen, carry cancer-predisposing genes, and lack protective factors. A combination of cancer-predisposing genes could be used as an intermediate risk marker rather than taking diagnosis of cancer as the endpoint. Such markers may include PAH-DNA adduct level and polymorphism in PAH-metabolizing enzymes such as the cytochrome P450 family member CYP1A1, the 4 S PAH-binding protein glutathione S-transferase (GSTM1), and cAMP-dependent protein kinase (Bhat et al. (1996) J. Biol. Chem. 271:32551–32556; and Bartsch, H. et al. (1998) Recent Results Cancer Res. 154:86–96). For example, Bartsch et al. (supra) showed that BPDE-DNA adduct levels in bronchial tissues of cigarette smokers with high CYP1A1 inducibility and inactive GSTM1 were approximately 100-fold higher than in smokers with an active GSTM 1.

Identification of genes that are expressed in response to polycyclic aromatic hydrocarbon exposure provides new diagnostic and therapeutic targets. The present invention satisfies a need in the art by providing new compositions that are useful for diagnosis, prognosis, treatment, prevention, and evaluation of therapies for cancer and its complications.

SUMMARY OF THE INVENTION

The invention provides for a substantially purified nucleic acid molecule comprising a gene that is expressed in response to polycyclic aromatic hydrocarbons (PAH). In one aspect, the nucleic acid molecule comprises a sequence selected from (a) a nucleic acid molecule which encodes the protein of SEQ ID NOs:6–8 or a portion thereof; (b) a nucleic acid molecule of SEQ ID NOs:1–5 or a fragment thereof; (c) a nucleic acid molecule complementary to the nucleic acid molecule of (a) or (b); (d) a probe which hybridizes to the nucleic acid molecule of (a), (b), or (c). In another aspect, the nucleic acid molecule comprises a sequence selected from (a) a nucleic acid molecule which encodes the protein of SEQ ID NO:14 or a portion thereof; (b) a nucleic acid molecule of SEQ ID NOS:9–13 or a fragment thereof; (c) a nucleic acid molecule complementary to the nucleic acid molecule of (a) or (b); (d) a probe which hybridizes to the nucleic acid molecule of (a), (b), or (c). The invention further provides an expression vector comprising any of the above described nucleic acid molecules and host cells comprising the expression vector. The invention still further provides a method for treating or preventing a disease or condition associated with the altered expression of a gene that is expressed in response to PAH comprising administering to a subject in need a nucleic acid molecule described above in an amount effective for treating or preventing the disease. The invention also provides a pharmaceutical composition comprising a nucleic acid molecule and a pharmaceutical carrier.

The invention additionally provides methods for using a nucleic acid molecule. One method uses the nucleic acid molecule to screen a library of molecules or compounds to identify at least one ligand which specifically binds the nucleic acid molecule and comprises combining the nucleic acid molecule with a library of molecules or compounds under conditions to allow specific binding and detecting specific binding, thereby identifying a ligand which specifically binds the nucleic acid molecule. In this first method, the library is selected from DNA molecules, RNA molecules, PNAs, mimetics, and proteins; and the ligand identified using the method may be used to modulate the activity of the nucleic acid molecule. A second method uses the nucleic acid molecule to purify a ligand which specifically binds the nucleic acid molecule and comprises combining the nucleic acid molecule with a sample under conditions to allow specific binding, detecting specific binding between the nucleic acid molecule and a ligand, recovering the bound nucleic acid molecule, and separating the nucleic acid molecule from the ligand, thereby obtaining purified ligand. A third method uses the nucleic acid molecule to diagnose a disease or condition associated with the altered expression of a gene that is expressed in response to PAH in a plurality of biological samples and comprises hybridizing a nucleic acid molecule to a sample under conditions to form one or more hybridization complexes, detecting the hybridization complexes, and comparing the levels of the hybridization complexes with the level of hybridization complexes in a non-diseased sample, wherein the altered level of hybridization complexes compared with the level of hybridization complexes of a non-diseased sample indicates the presence of the disease or condition.

A fourth method uses the nucleic acid molecule to produce a protein and comprises culturing a host cell containing an expression vector containing the nucleic acid molecule under conditions for expression of the protein and recovering the protein from cell culture.

The invention provides a substantially purified protein comprising the product of a gene that is expressed in response to PAH. The invention also provides a protein comprising (a) a protein selected from SEQ ID NOs:6–8 or a portion thereof; and (b) an oligopeptide comprising at least 6 sequential amino acids of the protein of (a). The invention further provides a protein comprising (a) a protein of SEQ ID NO:14 or a portion thereof; and (b) an oligopeptide comprising at least 6 sequential amino acids of the protein of (a). The invention also provides a pharmaceutical composition comprising a protein and a pharmaceutical carrier.

The invention additionally provides methods for using a protein. One method uses the protein to screen a library of molecules or compounds to identify at least one ligand which specifically binds the protein and comprises combining the protein with the library of molecules or compounds under conditions to allow specific binding and detecting specific binding between the protein and ligand, thereby identifying a ligand which specifically binds the protein. In this method, the library is selected from DNA molecules, RNA molecules, PNAs, mimetics, proteins, agonists, antagonists, and antibodies; and the ligand identified using the method is used to modulate the activity of the protein. A second method uses the protein to purify a ligand from a sample and comprises combining the protein with a sample under conditions to allow specific binding, detecting specific binding between the protein and a ligand, recovering the bound protein, and separating the protein from the ligand, thereby obtaining purified ligand. A third method uses the protein to treat or to prevent a disease associated with the altered expression of a gene that is expressed in response to PAH in a subject in need and comprises administering to the subject in need the pharmaceutical composition containing the polypeptide in an amount effective for treating or preventing the disease.

The invention provides an antibody or Fab comprising an antigen binding site, wherein the antigen binding site specifically binds to the protein. The invention also provides a method for treating or preventing a disease associated with the altered expression of a gene that is expressed in response to PAH in a subject in need, the method comprising the step of administering to the subject in need the antibody or the Fab in an amount effective for treating or preventing the disease. The invention further provides an immunoconjugate comprising the antigen binding site of the antibody or Fab joined to a therapeutic agent. The invention additionally provides a method for treating or preventing a disease associated with the altered expression of a gene that is coexpressed with one or more known atherosclerosis-associated genes in a subject in need, the method comprising the step of administering to the subject in need the immunoconjugate in an amount effective for treating or preventing the disease.

The invention also provides a method for detecting or diagnosing effect of a compound on expression level of at least one nucleic acid molecule in a subject and comprises treating the subject with the compound, obtaining a sample from the subject, contacting the sample with at least one nucleic acid molecule of SEQ ID NOs:9–13 or a fragment thereof under conditions for the formation of hybridization complexes, and detecting at least one hybridization complex, wherein the presence, absence, or change in amount of hybridization complex when compared with hybridization complex formed with a sample from an untreated subject indicates the effect of the compound. In this method, the compound is any compound which may have a genotoxic effect, such as polycyclic aromatic hydrocarbons, or a therapeutic which may ameliorate effects caused by a genotoxic compound.

BRIEF DESCRIPTION OF THE SEQUENCE LISTING, TABLE, AND FIGURES

The Sequence Listing provides exemplary sequences of genes expressed in adult rat exposed to benzo(a)pyrene, SEQ ID NOs:9–13, and homologous human nucleic acid molecules, SEQ ID NOs: 1–5, and human proteins, SEQ ID NOs:6–8. Each sequence is identified by a sequence identification number (SEQ ID NO) and by the Incyte ID number with which the sequence was first identified.

Table 1 shows the SEQ ID NO and Incyte ID number for nucleic acid molecules present in adult rat liver exposed to benzo(a)pyrene and absent from untreated (control) rat liver, the SEQ ID NO and Incyte ID number for the human nucleic acid homolog; the location of a unique region of the human nucleic acid molecule; the percent sequence identity between the rat sequence and corresponding human sequence determined using the LASERGENE program (DNASTAR, Madison Wis.); and the tissues where the human sequence is predominantly expressed.

FIGS. 1A, 1B, 1C, 1D, 1E, and 1F show the nucleic acid sequence of SEQ ID NO:1 and encoded amino acid sequence, SEQ ID NO:6. The alignment was produced using MACDNASIS PRO software (Hitachi Software Engineering, South San Francisco Calif.).

FIGS. 2A, 2B, and 2C show the nucleic acid sequence of SEQ ID NO:4 and encoded amino acid sequence, SEQ ID NO:7. The alignment was produced using MACDNASIS PRO software (Hitachi Software Engineering).

FIG. 3 shows the nucleic acid sequence, SEQ ID NO:5, and encoded amino acid sequence, SEQ ID NO:8. The alignment was produced using MACDNASIS PRO software (Hitachi Software Engineering).

FIG. 4 demonstrates the chemical and structural similarity between the human protein, SEQ ID NO:8, and the rat protein homolog, SEQ ID NO:14, produced using the MEGALIGN program (DNASTAR, Madison Wis.).

DESCRIPTION OF THE INVENTION

It must be noted that as used herein and in the appended claims, the singular forms "a", "an", and "the" include the plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Definitions

"NSEQ" refers generally to a polynucleotide sequence of the present invention, including SEQ ID NOs: 1–5 and 9–13. "PSEQ" refers generally to a protein sequence of the present invention, including SEQ ID NOs:6–8 and 14.

"Biologically active" refers to a protein having structural, immunological, regulatory, or chemical functions of a naturally occurring, recombinant or synthetic molecule.

"Complementary" refer to the natural hydrogen bonding by base pairing between purines and pyrimidines. For example, the sequence A—C—G—T forms hydrogen bonds with its complements T—G—C—A or U—G—C—A. Two single-stranded molecules may be considered partially complementary, if only some of the nucleotides bond, or completely complementary, if nearly all of the nucleotides bond. The degree of complementarity between nucleic acid strands affects the efficiency and strength of the hybridization and amplification reactions.

"Derivative" refers to the chemical modification of a nucleic acid molecule or amino acid sequence. Chemical modifications can include replacement of hydrogen by an alkyl, acyl, or amino group or glycosylation, pegylation, or any similar process which retains or enhances biological activity or lifespan of the molecule or sequence.

"Fragment" refers to an Incyte clone or any part of a nucleic acid molecule which retains a usable, functional characteristic. Useful fragments include oligonucleotides which may be used in hybridization or amplification technologies or in regulation of replication, transcription or translation.

"Gene" or "gene sequence" refers to the partial or complete coding sequence of a gene, its complement, and its 5' or 3' untranslated regions.

"Homology" refers to sequence similarity between a reference sequence and at least a fragment of a newly sequenced clone insert or its encoded amino acid sequence.

"Hybridization complex" refers to a complex between two nucleic acid molecules by virtue of the formation of hydrogen bonds between purines and pyrimidines.mation of hydrogen bonds between purines and pyrimidines.

"Ligand" refers to any molecule, agent, or compound which will bind specifically to a complementary site on a nucleic acid molecule or protein. Such ligands stabilize or modulate the activity of nucleic acid molecules or proteins of the invention and may be composed of at least one of the following: inorganic and organic substances including nucleic acids, proteins, carbohydrates, fats, and lipids.

"Modulates" refers to a change in activity (biological, chemical, or immunological) or lifespan resulting from specific binding between a molecule and either a nucleic acid molecule or a protein.

"Nucleic acid molecule" refers to a oligonucleotide, polynucleotide or any fragment thereof. It may be DNA or RNA of genomic or synthetic origin, double-stranded or single-stranded, and combined with carbohydrate, lipids, protein, or other materials to perform a particular activity such as transformation or form a useful composition such as a peptide nucleic acid (PNA). "Oligonucleotide" is substantially equivalent to the terms amplimer, primer, oligomer, element, target, and probe and is preferably single stranded.

"Portion", as used herein, refers to any part of a protein used for any purpose, but especially for the screening of a library of molecules which specifically bind to that portion or for the production of antibodies.

"Protein" refers to an amino acid sequence, oligopeptide, peptide, polypeptide or portions thereof whether naturally occurring or synthetic.

"Sample" is used in its broadest sense. A sample containing nucleic acid molecules may comprise a bodily fluid; an extract from a cell, chromosome, organelle, or membrane isolated from a cell; genomic DNA, RNA, or cDNA in solution or bound to a substrate; a cell; a tissue; a tissue print; a forensic sample; and the like.

"Substantially purified" refers to nucleic acid molecules or proteins that are removed from their natural environment and are isolated or separated, and are at least about 60% free, preferably about 75% free, and most preferably about 90% free, from other components with which they are naturally associated.

"Substrate" refers to any rigid or semi-rigid support to which nucleic acid molecules or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

Detailed Description

Sequences in the present invention were identified by first comparing nucleic acid molecules expressed in benzo(a) pyrene-treated rat liver cDNA libraries to nucleic acid molecules expressed in untreated (control) rat liver cDNA libraries. The abundance sort program of the invention described in U.S. Pat No. 5,840,484 entitled "Comparative Gene Transcript Analysis", incorporated herein by reference, was used to tabulate and sort by frequency the MRNA transcripts corresponding to each gene identified in treated and untreated rat liver tissues. Transcript analysis summarized the presence and abundance of exact, unique, and homologous transcripts which were specific to treated or untreated tissue.

Nucleic acid molecules present only in benzo(a)pyrene-treated rat liver were used to identify homologous sequences from human. The human nucleic acid molecules, SEQ ID NOs:1–5, and proteins, SEQ ID NOs:68; and rat nucleic acid molecules, SEQ ID NOs:9–13, and protein, SEQ ID NO:14; are provided in the Sequence Listing. Since the nucleic acid molecules were identified solely based on differential expression in treated versus untreated tissue, it is not essential to know a priori the name, structure, or function of a particular gene or protein. The usefulness of the human sequences exists in their immediate value as diagnostics for cancer, and of the rat sequences, in assays to test PAH molecules or compounds for genotoxic or other effects.

Table 1 shows the nucleic acid molecules present in benzo(a)pyrene-treated rat liver and absent in untreated rat liver, SEQ ID NOs:8–13, and their human homologs, SEQ ID NOs:1–5. Columns 1 and 2 list the SEQ ID NO and Incyte ID number, respectively, for each rat nucleic acid molecule, SEQ ID NOs:8–13, present in benzo(a)pyrene-treated liver and absent in untreated liver. These nucleic acid molecules were used to identify the human nucleic acid molecules shown in columns 3 and 4. Columns 3 and 4 list the SEQ ID NO and Incyte ID number, respectively, for each human nucleic acid molecule. Column 5 shows exemplary unique fragments of SEQ ID NOs: 1–5. Such fragments of SEQ ID NOs:1–5 are useful in hybridization or amplification technologies to identify changes in expression pattern of the same or similar sequences. Column 5 shows the sequence identity between the rat nucleic acid molecule in column I and the corresponding human nucleic acid molecule in column 3. Column 6 identifies the human tissues where the nucleic acid molecules in column 3 are predominantly expressed. Of particular note, SEQ ID NO:1, SEQ ID NO:3, and SEQ ID NO:4 are expressed in reproductive tissues, SEQ ID NO:4 is expressed in hematopoietic/immune tissues, and SEQ ID NO:5 is expressed in liver tissue.

The invention encompasses the human nucleic acid molecule of SEQ ID NO:1 (Incyte ID number 1851405) which encodes the protein of SEQ ID NO:6, as shown in FIGS. 1A–F. The protein of SEQ ID NO:6 is 587 amino acids in length and has five N-glycosylation sites at residues N7, N361, N371, and N484; twelve casein kinase II phosphorylation sites at residues S25, S40, S100, S121, T147, S189, S194, S336, T347, S413, S486, and T497; thirteen protein kinase C phosphorylation sites at residues S25, S73, T123, T168, S169, T323, S336, T368, S418,S 469, S486, T514, and T521; and a tyrosine kinase phosphorylation site at residue Y496.

The invention also encompasses the human nucleic acid molecule of SEQ ID NO:4 (Incyte ID number 2009569) which encodes the protein of SEQ ID NO:7, as shown in FIGS. 2A–C. The protein of SEQ ID NO:7 is 218 amino acids in length and has a signal peptide from residue M1 to residue G54; one N-glycosylation site at residue N82; seven casein kinase II phosphorylation sites at residues T50, S61, S65, S140, S197, T206, and T212; five protein kinase C phosphorylation sites at residues S98, T107, T133, S167, and 7212; and a tyrosine kinase phosphorylation site at residue Y115.

The invention further encompasses the human nucleic acid molecule of SEQ ID NO:5(Incyte ID number 1642580) which encodes the protein of SEQ ID NO:8, as shown in FIG. 3. The protein of SEQ ID NO:8 is 85 amino acids in length and has a signal peptide from residue M1 to G24; and a cAMP- and cGMP-dependent protein kinase phosphorylation site at residue T61. Rat nucleic acid molecule SEQ ID NO:13, first identified as present in benzo(a)pyrene-treated rat liver and absent from untreated rat liver, encodes the protein of SEQ ID NO:14. As shown in FIG. 4, human protein SEQ ID NO:8 and rat homolog SEQ ID NO: 14 share 49% identity, the signal peptide, and the cAMP- and cGMP-dependent protein kinase phosphorylation site.

Therefore, the invention provides nucleic acid molecules (NSEQ) comprising SEQ ID NOs:1–5 and fragments thereof; and SEQ ID NOs:9–13 and fragments thereof. These ten nucleic acid molecules are shown by the method of the present invention to have strong differential expression associated with response to benzo(a)pyrene exposure. The invention also encompasses a complement of the nucleic acid molecule. The nucleic acid molecules are useful for screening libraries of molecules or compounds for specific binding and for diagnosis and prognosis of disorders associated with cancer and its complications.

The nucleic acid molecules are particularly useful when they are hybridizable array elements in a microarray. Such a microarray can be employed to monitor the expression of genes which are differentially expressed in normal, diseased, or cancerous tissues. The microarray can be used in large scale genetic or gene expression analysis of a large number of nucleic acid molecules; in the diagnosis of disorders before phenotypic symptoms are evident; or in the differential diagnosis of disorders with similar symptoms. The microarray can also be used in the monitoring and evaluation of treatments where altered expression of genes coding for proteins implicated in carcinogen exposure cause a disorder, such as cancer. Additionally, the microarray can be used to investigate an individual's predisposition to a disorder or progress after diagnosis. Furthermore, the microarray can be employed to investigate cellular responses, such as cell proliferation, transformation, and the like.

When the nucleic acid molecules of the invention are employed as hybridizable array elements in a microarray, the array elements are organized in an ordered fashion so that each element is present at a specified location on the substrate. Because the array elements are at specified locations on the substrate, the hybridization patterns and intensities (which together create a unique expression profile) can be interpreted in terms of expression levels of particular genes and can be correlated with a particular disease, condition, or treatment.

The invention also entails a pharmaceutical composition comprising a nucleic acid molecule of the invention in conjunction with a suitable pharmaceutical carrier and a method for treating or preventing a disorder or condition associated with altered expression of genes that respond to genotoxic compounds comprising administering to a subject in need such a composition in an amount effective for treating or preventing a disorder or condition associated with exposure to genotoxic compounds.

NSEQ or the encoded PSEQ were searched against the GenBank primate (pri), rodent (rod), mammalian (mam), vertebrate (vrtp), and eukaryote (eukp) databases, SwissProt, BLOCKS (Bairoch et al. (1997) Nucleic Acids Res. 25:217–221), PFAM, and other databases that contain previously identified and annotated motifs, sequences, and gene functions. Methods that search for primary sequence patterns with secondary structure gap penalties (Smith et al. (1992) Protein Engineering 5:35–51) as well as algorithms such as Basic Local Alignment Search Tool (BLAST; Altschul, S. F. (1993) J. Mol. Evol. 36:290–300; Altschul et al. (1990) J. Mol. Biol. 215:403–410), BLOCKS (Henikoff, S. and Henikoff, G. J. (1991) Nucleic Acids Research 19:6565–6572), Hidden Markov Models (HMM; Eddy, S. R. (1996) Cur. Opin. Str. Biol. 6:361–365; Sonnhammer et al. (1997) Proteins 28:405–420), and the like, can be used to manipulate and analyze nucleotide and amino acid sequences. These databases, algorithms and other methods are well known in the art and are described in Ausubel et al. (1997; *Short Protocols in Molecular Biology*, John Wiley & Sons, New York N.Y., unit 7.7) and in Meyers, R. A. (1995; *Molecular Biology and Biotechnology*, Wiley VCH, New York N.Y., p 856–863).

Also encompassed by the invention are nucleic acid molecules that are capable of hybridizing to SEQ ID NOs: 1–5, SEQ ID NOs:9–13, and fragments thereof under stringent conditions. Stringent conditions can be defined by salt concentration, temperature, and other chemicals and conditions well known in the art. Suitable conditions can be selected, for example, by varying the concentrations of salt in the prehybridization, hybridization, and wash solutions or by varying the hybridization and wash temperatures. With some substrates, the temperature can be decreased by adding formamide to the prehybridization and hybridization solutions.

Hybridization can be performed at low stringency with buffers, such as 5×SSC with 1% sodium dodecyl sulfate (SDS) at 60° C., which permits complexes to form between two nucleic acid sequences that contain some mismatches. Subsequent washes are performed at higher stringency with buffers such as 0.2×SSC with 0.1% SDS at either 45° C. (medium stringency) or 68° C. (high stringency), to maintain hybridization of only those complexes that contain completely complementary sequences. Background signals can be reduced by the use of detergents such as SDS, Sarcosyl, or Triton X- 100, and/or a blocking agent, such as salmon sperm DNA. Hybridization methods are described in detail in Ausubel (supra, units 2.8–2.11, 3.18–3.19 and 4–6–4.9) and Sambrook et al. (1989; *Molecular Cloning A Laboratory Manual*, Cold Spring Harbor Press, Plainview N.Y.)

NSEQ can be extended utilizing a partial nucleotide sequence and employing various PCR-based methods known in the art to detect upstream sequences such as promoters and other regulatory elements. (See, e.g., Dieffenbach, C. W. and G. S. Dveksler (1995) *PCR Primer, a Laboratory Manual*, Cold Spring Harbor Press, Plainview N.Y.). Additionally, one may use an XL-PCR kit (PE Biosystems, Foster City Calif.), nested primers, and commercially available cDNA (Life Technologies, Rockville Md.) or genomic libraries (Clontech, Palo Alto Calif.) to extend the sequence. For all PCR-based methods, primers may be designed using commercially available software, such as OLIGO 4.06 software (National Biosciences, Plymouth Minn.) or another appropriate program, to be about 18 to 30 nucleotides in length, to have a GC content of about 50%, and to form a hybridization complex at temperatures of about 68° C. to 72° C.

In another aspect of the invention, NSEQ can be cloned in recombinant DNA molecules that direct the expression of PSEQ or structural or functional portions thereof, in appropriate host cells. Due to the inherent degeneracy of the genetic code, other DNA sequences which encode substantially the same or a functionally equivalent protein may be produced and used to express the protein encoded by NSEQ. The nucleic acid molecules of the present invention can be engineered using methods generally known in the art in order to alter the nucleotide sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In order to express a biologically active protein, NSEQ, or derivatives thereof, may be inserted into an appropriate expression vector, i.e., a vector which contains the necessary elements for transcriptional and translational control of the inserted coding sequence in a particular host. These elements include regulatory sequences, such as enhancers, constitutive and inducible promoters, and 5' and 3' untranslated regions. Methods which are well known to those skilled in the art may be used to construct such expression vectors. These methods include in vitro recombinant DNA techniques, synthetic techniques, and in vivo genetic recombination. (See, e.g., Sambrook, supra, and Ausubel, supra).

A variety of expression vector/host cell systems may be utilized to express NSEQ. These include, but are not limited to, microorganisms such as bacteria transformed with recombinant bacteriophage, plasmid, or cosmid DNA expression vectors; yeast transformed with yeast expression vectors; insect cell systems infected with baculovirus vectors; plant cell systems transformed with viral or bacterial expression vectors; or animal cell systems. For long term production of recombinant proteins in mammalian systems, stable expression in cell lines is preferred. For example, NSEQ can be transformed into cell lines using expression vectors which may contain viral origins of replication and/or endogenous expression elements and a selectable or visible marker gene on the same or on a separate vector. The invention is not to be limited by the vector or host cell employed.

In general, host cells that contain NSEQ and that express PSEQ may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences. Immunological methods for detecting and measuring the expression of PSEQ using either specific polyclonal or monoclonal antibodies are known in the art. Examples of such techniques include enzyme-linked immunosorbent assays (ELISAs), radioimmunoassays (RIAs), and fluorescence activated cell sorting (FACS).

Host cells transformed with NSEQ may be cultured under conditions suitable for the expression and recovery of the protein from cell culture. The protein produced by a transgenic cell may be secreted or retained intracellularly depending on the sequence and/or the vector used. As will be understood by those of skill in the art, expression vectors containing NSEQ may be designed to contain signal sequences which direct secretion of the protein through a prokaryotic or eukaryotic cell membrane.

In addition, a host cell strain may be chosen for its ability to modulate expression of the inserted sequences or to process the expressed protein in the desired fashion. Such modifications of the protein include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK 293, and W138) are available from the American Type Culture Collection (ATCC, Bethesda Md.) and may be chosen to ensure the correct modification and processing of the expressed protein.

In another embodiment of the invention, natural, modified, or recombinant nucleic acid molecules are ligated to a heterologous sequence resulting in translation of a fusion protein containing heterologous protein moieties in any of the aforementioned host systems. Such heterologous protein moieties facilitate purification of fusion proteins using commercially available affinity matrices. Such moieties include, but are not limited to, glutathione S-transferase, maltose binding protein, thioredoxin, calmodulin binding peptide, 6-His, FLAG, c-myc, hemaglutinin, and monoclonal antibody epitopes.

In another embodiment, the nucleic acid molecules are synthesized, in whole or in part, using chemical or enzymatic methods well known in the art (Caruthers et al. (1980) Nucleic Acids Symp. Ser. (7):215–233; Ausubel, supra). For example, peptide synthesis can be performed using various solid-phase techniques (Roberge et al. (1995) Science 269:202–204), and synthesis can be automated using machines such as the ABI 431 A peptide synthesizer (PE Biosystems). If desired, the amino acid sequence may be altered during synthesis and/or combined with sequences from other proteins to produce a variant protein.

In another embodiment, the invention entails substantially purified proteins (PSEQ) of SEQ ID NOs:6–8, SEQ ID NO:14, or portions thereof.

Screening, Diagnostic and Therapeutics

The nucleic acid molecules can be used in selection and evaluation of therapeutic molecules, diagnosis, prognosis, prevention, and treatment for cancer and its complications.

The nucleic acid molecules may be used to screen a library of molecules or compounds for specific binding. The assay can be used to screen a library of DNA molecules, RNA molecules, PNAs, peptides, ribozymes, antibodies, agonists, antagonists, immunoglobulins, inhibitors, proteins including transcription factors, enhancers, repressors, and drugs and the like which regulate the activity of the nucleic acid molecule in the biological system. The assay involves providing a library of molecules or compounds, combining the nucleic acid molecule or a fragment thereof with the library under conditions to allow specific binding, and detecting specific binding to identify at least one molecule which specifically binds the polynucleotide sequence.

Similarly the protein or a portion thereof may be used to screen libraries of molecules or compounds in any of a variety of screening assays. The portion of the protein employed in such screening may be free in solution, affixed to an abiotic or biotic substrate (e.g., borne on a cell surface), or located intracellularly. Specific binding between the polypeptide and molecule may be measured. The assay can be used to screen a library of DNA molecules, RNA molecules, PNAs, peptides, ribozymes, antibodies, agonists, antagonists, immunoglobulins, inhibitors, peptides, proteins, drugs and the like, which specifically bind the polypeptide. One method for high throughput screening using very small assay volumes and very small amounts of test compound is described in Burbaum et al. U.S. Pat. No. 5,876,946, incorporated herein by reference, which screens large numbers of molecules for enzyme inhibition or receptor binding.

In one preferred embodiment, the nucleic acid molecules are used for diagnostic purposes to determine absence, presence, and excess gene expression. The polynucleotides may be at least 18 nucleotides long and consist of complementary RNA and DNA molecules, branched nucleic acids, and/or peptide nucleic acids (PNAs). In one alternative, the nucleic acid molecules are used to detect and quantify gene expression in samples in which expression of NSEQ is correlated with disease. In another alternative, NSEQ can be used to detect genetic polymorphisms associated with a disease. These polymorphisms may be detected in the transcript cDNA.

The specificity of the probe is determined by whether it is made from a unique region, a regulatory region, or from a conserved motif. Both probe specificity and the stringency of diagnostic hybridization or amplification (maximal, high, intermediate, or low) will determine whether the probe identifies only naturally occurring, exactly complementary sequences, allelic variants, or related sequences. Probes designed to detect related sequences should preferably have at least 70% sequence identity to any of the nucleic acid molecules encoding PSEQ.

Methods for producing hybridization probes include the cloning of nucleic acid molecules into vectors for the production of mRNA probes. Such vectors are known in the art, are commercially available, and may be used to synthesize RNA probes in vitro by adding appropriate RNA polymerases and labeled nucleotides. Hybridization probes may incorporate nucleotides labeled by a variety of reporter groups including, but not limited to, radionuclides such as $^{32}P$ or $^{35}S$, enzymatic labels such as alkaline phosphatase coupled to the probe via avidin/biotin coupling systems, fluorescent labels, and the like. The labeled nucleic acid molecules may be used in Southern or northern analysis, dot blot, or other membrane-based technologies; in PCR technologies; and in microarrays utilizing samples from subjects to detect altered NSEQ expression.

NSEQ can be labeled by standard methods and added to a sample from a subject under conditions suitable for the formation and detection of hybridization complexes. After incubation the sample is washed, and the signal associated with hybrid complex formation is quantitated and compared with a standard value. Standard values are derived from any control sample, typically one that is free of the suspect disease. If the amount of signal in the subject sample is altered in comparison to the standard value, then the presence of altered levels of expression in the sample indicates the presence of the disease. Qualitative and quantitative methods for comparing the hybridization complexes formed in subject samples with previously established standards are well known in the art.

Such assays may also be used to evaluate the efficacy of a particular therapeutic treatment regimen in animal studies, in clinical trials, or to monitor the treatment of an individual subject. Once the presence of disease is established and a treatment protocol is initiated, hybridization or amplification assays can be repeated on a regular basis to determine if the level of expression in the subject begins to approximate that which is observed in a healthy subject. The results obtained from successive assays may be used to show the efficacy of treatment over a period ranging from several days to many years. Further, the nucleic acid molecules may be used for the diagnosis of a variety of diseases which may be induced through exposure to genotoxic agents.

The nucleic acid molecules may also be used as targets in a microarray. The microarray can be used to monitor the expression patterns of large numbers of genes simultaneously and to identify splice variants, mutations, and polymorphisms. Information derived from analyses of the expression patterns may be used to determine gene function, to understand the genetic basis of a disease, to diagnose a disease, and to develop and monitor the activities of therapeutic agents used to treat a disease. Microarrays may also be used to detect genetic diversity, such as single nucleotide polymorphisms which may characterize a particular population, at the genome level.

In yet another alternative, nucleic acid molecules may be used to generate hybridization probes useful in mapping the naturally occurring genomic sequence. Fluorescent in situ hybridization (FISH) may be correlated with other physical chromosome mapping techniques and genetic map data as described in Heinz-Ulrich et al. (In: Meyers, R. A. (1995) *Molecular Biology and Biotechnology*, Wiley VCH Publishers, New York N.Y., pp. 965–968).

In another embodiment, antibodies or antibody fragments comprising an antigen binding site that specifically binds PSEQ may be used for the diagnosis of diseases characterized by the over-or-under expression of PSEQ. A variety of protocols for measuring PSEQ, including ELISAs, RIAs, and FACS, are well known in the art and provide a basis for diagnosing altered or abnormal levels of expression. Standard values for PSEQ expression are established by combining samples taken from healthy subjects, preferably human, with antibody to PSEQ under conditions suitable for complex formation. The amount of complex formation may be quantitated by various methods, preferably by photometric means. Quantities of PSEQ expressed in disease samples are compared with standard values. Deviation between standard and subject values establishes the parameters for diagnosing or monitoring disease. Alternatively, one may use competitive drug screening assays in which neutralizing antibodies capable of binding PSEQ specifically compete with a test compound for binding the protein. Antibodies can be used to detect the presence of any peptide which shares one or more antigenic determinants with PSEQ. In one aspect, the anti-PSEQ antibodies of the present invention can be used for treatment or monitoring therapeutic treatment for diseases associated with exposure to genotoxic agents.

In another aspect, the NSEQ, or its complement, may be used therapeutically for the purpose of expressing mRNA and protein, or conversely to block transcription or translation of the mRNA. Expression vectors may be constructed using elements from retroviruses, adenoviruses, herpes or vaccinia viruses, or bacterial plasmids, and the like. These vectors may be used for delivery of nucleotide sequences to a particular target organ, tissue, or cell population. Methods well known to those skilled in the art can be used to construct vectors to express nucleic acid molecules or their complements. (See, e.g., Maulik et al. (1997) *Molecular Biotechnology Therapeutic Applications and Strategies*, Wiley-Liss, New York N.Y.) Alternatively, NSEQ, or its complement, may be used for somatic cell or stem cell gene therapy. Vectors may be introduced in vivo, in vitro, and ex vivo. For ex vivo therapy, vectors are introduced into stem cells taken from the subject, and the transgenic cells are clonally propagated for autologous transplant back into that same subject. Delivery of NSEQ by transfection, liposome injections, or polycationic amino polymers may be achieved using methods which are well known in the art. (See, e.g., Goldman et al. (1997) Nature Biotechnology 15:462–466.) Additionally, endogenous NSEQ expression may be inactivated using homologous recombination methods which insert an inactive gene sequence into the coding region or other appropriate targeted region of NSEQ. (See, e.g. Thomas et al. (1987) Cell 51: 503–512.)

Vectors containing NSEQ can be transformed into a cell or tissue to express a missing protein or to replace a nonfunctional protein. Similarly a vector constructed to express the complement of NSEQ can be transformed into a cell to downregulate the overexpression of PSEQ. Complementary or antisense sequences may consist of an oligonucleotide derived from the transcription initiation site; nucleotides between about positions −10 and +10 from the ATG are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee el al. In: Huber, B. E. and B. I. Carr (1994) *Molecular and Immunologic Approaches*, Futura Publishing, Mt. Kisco N.Y., pp. 163–177.)

Ribozymes, enzymatic RNA molecules, may also be used to catalyze the cleavage of mRNA and decrease the levels of particular mRNAs, such as those comprising the nucleic acid molecules of the invention. (See, e.g. Rossi (1994) Current Biology 4:469–471.) Ribozymes may cleave mRNA at specific cleavage sites. Alternatively, ribozymes may cleave mRNAs at locations dictated by flanking regions that form complementary base pairs with the target mRNA. The construction and production of ribozymes is well known in the art and is described in Meyers (supra).

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiester linkages within the backbone of the molecule. Alternatively, nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases, may be included.

Further, an antagonist, or an antibody that binds specifically to PSEQ may be administered to a subject to treat or prevent a disease which may be induced through exposure to genotoxic agents. The antagonist, antibody, or fragment may be used directly to inhibit the activity of the protein or indirectly to deliver a therapeutic agent to cells or tissues which express the PSEQ. An immunoconjugate comprising a PSEQ binding site of the antibody or the antagonist and a therapeutic agent may be administered to a subject in need to treat or prevent disease. The therapeutic agent may be a cytotoxic agent selected from a group including, but not limited to, abrin, ricin, doxorubicin, daunorubicin, taxol, ethidium bromide, mitomycin, etoposide, tenoposide, vincristine, vinblastine, colchicine, dihydroxy anthracin dione, actinomycin D, diphteria toxin, Pseudomonas exotoxin A and 40, radioisotopes, and glucocorticoid.

Antibodies to PSEQ may be generated using methods that are well known in the art. Such antibodies may include, but are not limited to, polyclonal, monoclonal, chimeric, and single chain antibodies, Fab fragments, and fragments produced by a Fab expression library. Neutralizing antibodies, such as those which inhibit dimer formation, are especially preferred for therapeutic use. Monoclonal antibodies to PSEQ may be prepared using any technique which provides for the production of antibody molecules by continuous cell lines in culture. These include, but are not limited to, the hybridoma, the human B-cell hybridoma, and the EBV-hybridoma techniques. In addition, techniques developed for the production of chimeric antibodies can be used. (See, e.g., Pound J. D. (1998) *Immunochemical Protocols*, Methods Mol. Biol. Vol. 80). Alternatively, techniques described for the production of single chain antibodies may be employed. Antibody fragments which contain specific binding sites for PSEQ may also be generated. Various immunoassays may be used to identify antibodies having the desired specificity. Numerous protocols for competitive binding or immunoradiometric assays using either polyclonal or monoclonal antibodies with established specificities are well known in the art.

Yet further, an agonist of PSEQ may be administered to a subject to treat or prevent a disease associated with decreased expression, longevity or activity of PSEQ.

Pharmaceutical compositions are those substances wherein the active ingredients are contained in an effective amount to achieve a desired and intended purpose. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of protein or inhibitor which ameliorates the symptoms or condition. Therapeutic efficacy and toxicity of such agents may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it may be expressed as the ratio, $LD_{50}/ED_{50}$. Pharmaceutical compositions which exhibit large therapeutic indexes are preferred. The data obtained from cell culture assays and animal studies are used in formulating a range of dosage for human use.

EXAMPLES

It is to be understood that this invention is not limited to the particular devices, machines, materials and methods described. Although particular embodiments are described, equivalent embodiments may be used to practice the invention. The described embodiments are not intended to limit the scope of the invention which is limited only by the appended claims. The examples below are provided to enable the subject invention and are not included for the purpose of limiting the invention. For purposes of example, the preparation of the benzo(a)pyrene-treated rat liver cDNA library, RALITXT06, is described.

I cDNA Library Construction

The rat liver cDNA library, RALITXT06, was constructed from liver tissue removed from a male Sprague Dawley rat (Chrysalis International, Olyphant Pa.) who was seven-weeks old at treatment initiation. The rat was treated with benzo(a)pyrene, 10 mg/kg body weight in dimethyl sulfoxide at less than 2 ml/kg body weight by intraperitoneal injection and dosed three times per week for two weeks. The animal, euthanized by $CO_2$ inhalation, was sacrificed three days following the last dose.

The frozen tissue was homogenized and lysed in TRIZOL reagent (0.6 g tissue/12 ml TRIZOL; Life Technologies) using a POLYTRON homogenizer (PT-3000; Brinkmann Instruments, Westbury N.Y.). The homogenate was centrifuged, and the supernatant was decanted into a fresh tube and incubated briefly at 15–30° C. After chloroform was added (1:5 v/v chloroform:homogenate), the mixture was shaken vigorously by hand and incubated briefly at 15–30° C. The phases were separated by centrifugation, and the aqueous phase was removed to a fresh tube, mixed with isopropanol and a high salt precipitation solution (0.8M sodium citrate, 1.2M sodium chloride). Samples were incubated at 15–30° C. and centrifuged to collect RNA precipitate. The RNA pellet was washed twice with 75% ethanol, resuspended in 0.3M sodium acetate and 2.5 volumes 100% ethanol, and centrifuged. The RNA was washed twice with 75% ethanol and dissolved in DEPC-treated water.

The mRNA was isolated using the OLIGOTEX kit (Qiagen, Valencia Calif.) and used to construct the cDNA library. The mRNA was treated twice with DNaseI for 45 minutes at 25° C., precipitated using sodium acetate and ethanol, washed twice with 75% ethanol, and dissolved in DEPC-treated water. The mRNA was annealed to an oligo d(T) primer containing a NotI restriction enzyme site designed to prime the first strand cDNA synthesis at the poly(A) tail of mRNAs. This primer-adaptor contains d(T) residues and restriction endonuclease recognition sites. Three loc-doc primers (Biosource International, Camarillo Calif.) were synthesized. Each had the same NotI-oligo d(T) primer-adaptor except for a single non-thymine base after the poly(T) segment. This introduced base served to reduce the length of the cloned poly(A) tail. First strand cDNA synthesis was performed using 500 units of MMLV RT (Amersham Pharmacia Biotech) mixed with 50 units of AMV RT (Promega, Madison Wis.) in the presence of 4 mM sodium pyrophosphate and nucleotide substrates. After cDNA synthesis and ligation to EcoRI adaptors, the product was digested with NotI (New England Biolabs). The cDNAs were fractionated on a SEPHAROSE CL-4B column (Amersham Pharmacia Biotech), and those cDNAs exceeding 400 bp were ligated into the NotI and EcoRI sites of the pINCY 1 plasmid (Incyte Pharmaceuticals, Palo Alto Calif.). The plasmid was transformed into ELECTROMAX DH 10B cells (Life Technologies).

II Isolation and Sequencing of CDNA Clones

DNA was isolated using the following protocol. Single bacterial colonies were transferred into individual wells of 384-well plates (Genetix Ltd, Christchurch UK) using sterile toothpicks. The wells contained 65 µl of sterile Terrific Broth (Life Technologies) with 25 mg/1 carbenicillin and 0.4% glycerol (v/v). The plates were covered and placed in a Thermodyne incubator (Newtown Square Pa.) at 37° C. for 8–10 hours prior to use. Plasmid DNA was released from the cells and amplified using direct link PCR (Rao, V. B. (1994) Anal. Biochem. 216:1–14). The direct link PCR solution included 30 ml of NUCLEIX PLUS PCR nucleotide mix (Amersham Pharmacia Biotech), 300 µl of Taq DNA polymerase (Amersham Pharmacia Biotech) and 6 µl Pfu DNA polymerase (Stratagene). Five microliters of PCR solution were added to each of the 384 wells using the HYDRA 96-well microdispenser system (Robbins Scientific, Sunnyvale Calif.). The plates were centrifuged at 1000 rpm for 20 seconds and refrigerated until use. A 384 pin tool (V&P Scientific, San Diego Calif.) was used to transfer bacterial cells from the incubation plate into the plate containing the PCR solution and 0.1 % Tween 20 which lysed the cells and released the plasmid DNA. After lysis, the plates were covered with a cycle sealer, centrifuged up to 500 rpm, and cycled using a 384-well DNA ENGINE TETRAD thermal cycler (MJ Research, Watertown Ma.) using the program dPCR30 with the following parameters: Step 1) 95° C., 1 minute; Step 2) 94° C., 30 seconds; Step 3) 55° C., 30 seconds; Step 4) 72° C., 2 minutes; Step 5) steps 2,3, and 4 repeat 29 times; minutes; and Step 7) storage at 4° C.

The concentration of DNA in each well was determined by dispensing 100 µl PICOGREEN quantitation reagent (0.25% reagent (Molecular Probes, Eugene Oreg.) dissolved in TE) and 0.5 µl of undiluted PCR product into each well of an opaque fluorimeter plate (Corning Costar, Acton Mass.) and allowing the DNA to bind to the reagent. The plate was scanned in a Fluoroskan II (Labsystems Oy, Helsinki, Finland) to measure the fluorescence of the sample and to quantify the concentration of DNA.

The cDNAs were prepared using either a MICROLAB 2200 system (Hamilton) or a HYDRA microdispenser (Robbins Scientific, Sunnyvale Calif.) in combination with the DNA ENGINE peltier thermal cyclers (MJ Research) and sequenced by the method of Sanger, F. and A. R. Coulson (1975; J. Mol. Biol. 94:441–448) using an ABI PRISM 377 sequencing system (PE Biosystems). Most of the isolates were sequenced using standard ABI protocols and kits (Cat.# 79345, 79339, 79340, 79357, and 79355; PE Biosystems) at solution volumes of 0.25x–1.0 x. In the alternative, cDNAs were sequenced using solutions and dyes from Amersham Pharmacia Biotech.

III In Comparative Nucleic Acid Sequence Expression Analysis

Nucleic acid sequences, NSEQ, were first identified in rat tissue using electronic subtraction in ZOOSEQ 1.4 (Incyte Pharmaceuticals) to create a transcript image profile. Target tissues were benzo(a)pyrene-treated rat liver (RALITXT05 and RALITXT06) and background tissues were untreated (control) liver (RALINOTOI and RALINOT02). Transcript images for the rat tissues were compared using the following settings: Stringency $\geq 50$; product score cutoff $\leq 100$; and maximum results displayed ALL. Rat clones which were present in target tissue, but not in the background tissue, were recorded. In addition, rat clones which were present in background tissue, but not in target tissue, were recorded. The results included both annotated and unannotated clones. Unannotated clones and clones with annotation to any aspect of liver metabolism were selected. Selected clones were clustered and then assembled into contiguous sequences (contigs) using Phrap (P. Green, University of Washington) or GCG (Genetics Computer Group, Madison Wis.) fragment assembly systems. The rat contigs, SEQ ID NOs:9–13, were queried against LIFESEQ database (Incyte Pharmaceuticals) to identify homologous human nucleic acid molecules using BLAST with the following search parameters: Expected: 10; expected2: 0.15; Karlin and Atlschul sum statistics; and greedy spanning. Homologous human nucleic acid molecules were clustered and assembled using Phrap or GCG fragment assembly systems, as described above, to produce human contigs, SEQ ID NOs:1–5.

VI Homology Search

Nucleic acid molecules, SEQ ID NOs:1–5, and proteins, SEQ ID NOs:6–8, were queried against databases derived from sources such as GenBank and SwissProt. These databases, which contain previously identified and annotated sequences, were searched for regions of similarity using BLAST (Altschul, supra). BLAST matches that satisfied the probability thresholds of $10^{-25}$ or less for nucleotide sequences and $10^{-8}$ or less for polypeptide sequences were reported.

NSEQ and PSEQ were also analyzed for known motif patterns using MOTIFS, SPSCAN, BLIMPS, and HMM-based protocols. MOTIFS (Genetics Computer Group) searched sequences for patterns that matched those defined in the Prosite Dictionary of Protein Sites and Patterns (Bairoch supra), and displayed the patterns found and their corresponding literature abstracts. SPSCAN (Genetics Computer Group) searched for potential signal peptide sequences using a weighted matrix method (Nielsen et al. (1997) Prot. Eng. 10:1–6). Matches with a score of 5 or greater were considered. BLIMPS used a weighted matrix analysis algorithm to search for sequence similarity between SEQ ID NOs:6–8 and sequences in BLOCKS, a database consisting of short amino acid segments, or blocks of 3–60 amino acids in length, compiled from the PROSITE database (Henikoff; supra; Bairoch, supra) or PRINTS, a protein fingerprint database based on non-redundant sequences obtained from sources such as SwissProt, GenBank, PIR, and NRL-3D (Attwood et al. (1997) J. Chem. Inf. Comput. Sci. 37:417–424). For the purposes of the present invention, the BLIMPS searches reported matches with a cutoff score of 1000 or greater and a cutoff probability value of $1.0 \times 10^{-3}$. HMM-based protocols based on a probabilistic approach were searched for consensus primary structures of gene families in the protein sequences (Eddy, supra; Sonnhammer, supra).

VII Labeling of Probes and Hybridization Analyses

Polynucleotide sequences are isolated from a biological source and applied to a substrate suitable for standard nucleic acid hybridization protocols by one of the following methods. A mixture of target nucleic acids is fractionated by electrophoresis through an 0.7% agarose gel in 1xTAE (40 mM Tris acetate, 2 mM EDTA) running buffer and transferred to a nylon membrane by capillary transfer using 20x saline sodium citrate (SSC). Alternatively, the target nucleic acids are individually ligated to a vector and inserted into bacterial host cells to form a library. Target nucleic acids are arranged on a substrate by one of the following methods. In the first method, bacterial cells containing individual clones are robotically picked and arranged on a nylon membrane. The membrane is placed on bacterial growth medium, LB agar containing carbenicillin, and incubated at 37° C. for 16 hours. Bacterial colonies are denatured, neutralized, and digested with proteinase K. Nylon membranes are exposed to UV irradiation in a STRATALINKER UV-crosslinker (Stratagene, La Jolla Calif.) to cross-link DNA to the membrane.

In the second method, target nucleic acids are amplified from bacterial vectors by thirty cycles of PCR using primers complementary to vector sequences flanking the insert. Amplified target nucleic acids are purified using SEPHACRYL-400 columns (Amersham Pharmacia Biotech). Purified target nucleic acids are robotically arrayed onto a glass microscope slide previously coated with 0.05% aminopropyl silane (Sigma-Aldrich, St. Louis Mo.) and cured at 110° C. The arrayed glass slide (microarray) is exposed to UV irradiation in a STRATALINKER UV-crosslinker (Stratagene).

cDNA probe sequences are made from mRNA templates. Five micrograms of mRNA is mixed with 1 $\mu$g random primer (Life Technologies), incubated at 70° C. for 10 minutes, and lyophilized. The lyophilized sample is resuspended in 50 $\mu$l of 1xfirst strand buffer (CDNA Synthesis system; Life Technologies) containing a dNTP mix, $[\alpha\text{-}^{32}P]$ dCTP, dithiothreitol, and MMLV reverse transcriptase (Stratagene), and incubated at 42° C. for 1–2 hours. After incubation, the probe is diluted with 42 $\mu$l dH$_2$O, heated to 95° C. for 3 minutes, and cooled on ice. mRNA in the probe is removed by alkaline degradation. The probe is neutralized, and degraded mRNA and unincorporated nucleotides are removed using a PROBEQUANT G-50 microcolumn (Amersham Pharmacia Biotech). Probes can be labeled with fluorescent nucleotides, Cy3-dCTP or Cy5-CTP (Amersham Pharmacia Biotech) in place of the radiolabeled nucleotide, $[^{32}P]$dCTP.

Hybridization is carried out at 65° C. in a hybridization buffer containing 0.5 M sodium phosphate (pH 7.2), 7% SDS, and 1 mM EDTA. After the substrate is incubated in hybridization buffer at 65° C. for at least 2 hours, the buffer is replaced with 10 ml of fresh buffer containing the probe sequences. After incubation at 65° C. for 18 hours, the hybridization buffer is removed, and the substrate is washed sequentially under increasingly stringent conditions, up to 40 mM sodium phosphate, 1% SDS, 1 mM EDTA at 65° C. To detect signal produced by a radiolabeled probe hybridized on a membrane, the substrate is exposed to a PHOSPHORIMAGER cassette (Amersham Pharmacia Biotech), and the image is analyzed using IMAGEQUANT software (Amersham Pharmacia Biotech). To detect signals produced by a fluorescent probe hybridized on a microarray, the substrate is examined by confocal laser microscopy, and images are collected and analyzed using GEMTOOLS software (Incyte Pharmaceuticals).

VIII Production of Specific Antibodies

SEQ ID NOs:6–8, or portions thereof, substantially purified using polyacrylamide gel electrophoresis or other purification techniques, are used to immunize rabbits and to produce antibodies using standard protocols as described in Pound (supra).

Alternatively, the amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. Typically, oligopeptides 15 residues in length are synthesized using an ABI 431A peptide synthesizer (PE Biosystems) using Fmoc (9-fluorenylmethoxycarbonyl)-chemistry and coupled to keyhole limpet hemacyanin (KLH; Sigma-Aldxich) by reaction with N-maleimidobenzoyl-N-hydroxysuccinimide ester (Ausubel supra) to increase immunogenicity. Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XII Screening Molecules for Specific Binding with the Nucleic Acid Sequence or Protein The nucleic acid molecules, or fragments thereof, or the proteins, or portions thereof, are labeled with [$^{32}$P]-dCT?, Cy3-dCTP, Cy5-dCTP (Amersham Pharmacia Biotech), or BIODIPY or FITC (Molecular Probes, Eugene Oreg.), respectively. Libraries of candidate molecules; e.g., DNA molecules, RNA molecules, PNAs, peptides, proteins, mimetics, agonists, antagonists, antibodies, immunoglobulins, inhibitors, and drugs; previously arranged on a suitable substrate are incubated in the presence of labeled nucleic acid molecule or protein. After incubation for a suitable period under appropriate conditions for the nucleic acid molecule or protein, the substrate is washed, and any position on the substrate retaining label, which indicates specific binding or complex formation, is assayed, and the binding molecule is identified. Data obtained using different concentrations of the nucleic acid molecule or protein are used to calculate affinity between the labeled nucleic acid molecule or protein and the bound molecule.

TABLE 1

| Rat SEQ ID NO | Rat Incyte ID No. | Human SEQ ID NO. | Human Incyte ID No. | Unique Fragment | Identity | Human Tissue Expression Profile |
|---|---|---|---|---|---|---|
| 9 | 700062690 | 1 | 1851405 | 1587–1634 | 78.3% | 27% reproductive tissue, 15% nervous tissue, 14% cardiovascular, and 14% gastrointestinal tissues |
| 10 | 700140450 | 2 | 1991226 | 109–131 | 62.1% | 50% hematopoietic/immune tissue |
| 11 | 700367683 | 3 | 253053 | 690–740 | 61.3% | 31% reproductive tissue and 25% nervous tissue |
| 12 | 701316810 | 4 | 2009569 | 327–368 | 95.4% | 67% reproductive tissue |
| 13 | 700139271 | 5 | 1642580 | 196–231 | 49.3% | 44% liver tissue and 22% hematopoietic/immune tissue |

What is claimed is:

1. A substantially purified nucleic acid molecule expressed in response to polycyclic aromatic hydrocarbon exposure comprising:

(a) a nucleic acid molecule encoding a protein selected from SEQ ID NOs:7, 8 and 14;

(b) a nucleic acid molecule selected from the group consisting of SEQ ID NOs:1–5 and 9–13; or (c) a nucleic acid molecule which is the complement of the nucleic acid molecule of (a) or (b) wherein each and every nucleotide of the complement is complementary to each and every nucleotide of the nucleic acid molecule of (a) or (b).

2. A composition comprising at least one nucleic acid molecule of claim 1.

3. An expression vector comprising the nucleic acid molecule of claim 1.

4. A host cell comprising the expression vector of claim 3.

5. A method for producing a protein, the method comprising:

(a) culturing the host cell of claim 4 under conditions for expression of the protein; and (b) recovering the protein from cell culture.

6. A substantially purified nucleic acid molecule expressed in response to polycyclic aromatic hydrocarbon exposure comprising:

(a) a nucleic acid molecule encoding a protein of SEQ ID NOS:6; or (b) a nucleic acid molecule which is the complement of the nucleic acid molecule of (a) wherein each every nucleotide of the complement is complementary to each every nucleotide of the nucleic acid molecule of (a).

7. A composition comprising the nucleic acid molecule of claim 6.

* * * * *

SEQUENCE LISTING

<160> NUMBER OF SEQ ID NOS: 14

<210> SEQ ID NO 1
<211> LENGTH: 2439
<212> TYPE: DNA
<213> ORGANISM: Homo sapiens
<220> FEATURE:
<221> NAME/KEY:
<223> OTHER INFORMATION: 1851405
<300> PUBLICATION INFORMATION:

<400> SEQUENCE: 1

```
cttcagttcc tcgaagagat tcactttcaa aaacatcaac tccttataac aaatcaaaca      60
aagcagcaag ccaacaaggg accccatggg aaacacttgt cgtgtttgct atcaacttga     120
agcaattaaa cgttcaaatg aatatgagta atgtaatggg aaatacaact tggacaacta     180
gtggtttgaa gagccaggggc cgtctgtcag taggaagtaa tcgtgatcga gagatcagca     240
tgtctgttgg tctgggaaga tcacaattag attctaaagg aggagtagtt ggagggacca     300
tagatgtcaa tgctttggag atggttgctc atatttctga acatccaaat cagcaaccca     360
```

-continued

```
gtcacaaaat tcagattact atggggttcta ctgaagctcg tgttgattac atgggctcaa    420
gtatcctcat gggcatcttc agtaatgctg atcttaagct tcaggatgaa tggaaagtaa    480
acttgtataa tacattggat tcaagcataa ctgataaaag tgagattttc gtccatggag    540
atttgaagtg ggatattttc caagtaatga tatcaaggtc aaccacacca gatctgataa    600
aaataggaat gaagctccag gaattttttca cacaacaatt tgataccagc aaacgagctc    660
tgtctacctg gggaccagtt ccttaccttc cgccaaagac aatgactagc aacctagaaa    720
aaagttcaca agaacaatta cttgatgcag cacatcatcg cactggcct ggagtattga    780
aggtggtatc aggatgccac atatccttat ttcagattcc attaccagaa gatggaatgc    840
aatttggagg atcaatgagc ttacatgaa atcatatgac actggcatgt tttcatggtc    900
caaattttcg ttcaaaatct tgggcccttt ttcatttaga agaaccaaat attgcttttt    960
ggactgaagc tcagaaaatc tgggaagatg gctccagtga tcattctaca tatattgtac   1020
aaacactaga ttttcacctg ggtcataata ctatggttac caaaccatgt ggtgctttgg   1080
aaagtcctat ggcaacaata accaagataa caaggcgtcg ccatgaaaat ccaccccatg   1140
gagtagcaag tgtgaaagaa tggttcaatt atgttacagc tacaaggaat gaagagctaa   1200
atctgcttcg taatgttgat gctaacaaca ctgagaatag cactactgtg aagaattcta   1260
gtttgttgag tggattcaga ggaggttcta gctacaacca tgaaacagag actatctttg   1320
cattaccaag gatgcagctt gactttaaat ccattcatgt tcaagaacca caggagcctt   1380
cattacagga tgccagcctg aagccaaaag tagaatgtag tgtggtgaca gagttcactg   1440
accacatttg tgtgactatg gatgctgagc tcatcatgtt tcttcatgat ttagtatcag   1500
cttatcttaa agaaaaagaa aaagccatct ttccacctcg gattttatct actcgaccag   1560
gacaaaaaag tccaattatt atacatgacg acaattcctc tgataaagat agagaagata   1620
gcatcactta tactactgtg gactggagag attttatgtg caatacatgg cacctagaac   1680
ctactcttag attaatttct tggactggaa gaaagattga tccagtaggt gttgattata   1740
ttcttcaaaa attgggcttt catcatgcta ggactactat tcctaaatgg cttcaaagag   1800
gagtcatgga tccactggac aaggttctgt cagttcttat caaaaagctc ggtactgcac   1860
tacaggatga aaaggaaaag aaaggcaaag acaaagaaga acactaaaaa agtaatttga   1920
tctgtgaaca aattatgatt gtgtctgttt tattcactg gagtgttttt ttagtataat   1980
aatttgaaat ataactttaa aataattcta aatttgtggc tataattaaa agtttgtaag   2040
ttaacctgtt ctagttccat cattctgtgt acagtgaagt attgcatgat aatgtaaatt   2100
ttgtgaaaaa ctagattaaa atatataact gcttgttatg gtttataatt atataatgtg   2160
caatacaatt cctgcatctt taaaatgtct gcagaataac tgtgaatttt tttgttattg   2220
gattggccgt aacttttaga aaaaaatctt gttgatgata atgtgatttt ggggaggtca   2280
ttaattgctt tttctttttt aaatgtagac ttatataaat acctgtttgt atatagcttg   2340
agtaattgtg atatgattgt ataccactaa aatattgtta actattataa taaagtcaca   2400
gtaatggttt aaaaaagaaa aaagaaaaaa aaaaaaaaa                            2439
```

<210> SEQ ID NO 2
<211> LENGTH: 529
<212> TYPE: DNA
<213> ORGANISM: Homo sapiens
<220> FEATURE:
<221> NAME/KEY:
<223> OTHER INFORMATION: 1991226
<300> PUBLICATION INFORMATION:

<400> SEQUENCE: 2

```
ggacgctggc aaagcggggc agaccctgaa gactcactgc tcagcccagc gcccagatgt      60
ctgcaggtgg ctgagcccct tcatcctctc ctgctgcgtg tacttctgcc tctggattcc     120
cgaggaccag ctgtcctggt tcgctgccct ggtcaagtgc ctgcctgtcc tctgcctggc     180
tgggttcctg tgggtcatgt ccccaagcgg ggctacacc cagctcctcc agggagcct      240
tgtgtgctcg gctgtggggg acgcttgcct catctggccg gcagccttcg tccctggcat     300
ggccgccttt gccaccgccc acctcctcta cgtctgggcc ttcggcttct ctcccctgca     360
gcccggcctg ctgctgctca tcatcctggc ccctggcccc tactcagctt gtgctcagca     420
gctcgagccg gataggtctg cggtggagct atggctatct gatgcatctg tgcgggctgc     480
cacgtcgatg cgctgggcgg tgtctcacgt tctatggtgt gctggaact                529
```

<210> SEQ ID NO 3
<211> LENGTH: 2429
<212> TYPE: DNA
<213> ORGANISM: Homo sapiens
<220> FEATURE:
<221> NAME/KEY: unsure
<222> LOCATION: 2404, 2413, 2423, 2425, 2426
<223> OTHER INFORMATION: a or g or c or t, unknown, or other
<220> FEATURE:
<221> NAME/KEY:
<223> OTHER INFORMATION: 253053
<300> PUBLICATION INFORMATION:

<400> SEQUENCE: 3

```
ttatgtgttt aacctataaa tattggggtc ttctgtctaa actggggtca ctgttgcatg      60
gaacattgtt cttaatagtt gagaattgct tttttgaaaa ttttcatgaa ggaattttgg     120
taatgacttt gcttgcaggt tttttggggt gttttgagaa agtggcatgg aaacatgcag     180
tagttaatga gtttctcttg gtactgaaca ctattagaat atcattagtg atatttttc      240
tctttagagc attttaatg caactagccc ctatatttta atgtaagagt tactctgcaa     300
tctaagcaaa gcacccaaca atggtaaatg ttttttaaaa atgcagaact aagattttg      360
actctaaaga gagaaaatta caagggtgtt gccttatagc aaacccttgg gacaatcctt     420
catgtgagca aagtgttgat cttaatattg gttgtctgtg gtgtgctttt ttgtactgta     480
aaaatatgtg gttcatgtct aactctgctg tttattgtg gttgtggttc aagttttaa      540
tgtttaaagt tgatgctgtt ttcagaagag ctttttacta atttatttgt cagtgttccc     600
tatttgttac ttaaccatga tcctccagat tttttggagt attcttttct aaccttaacc     660
ctgccaaacc ttgatccatt ttgacatttg ttatgcacta ttttttatatc tctgtgagag    720
attttttccaa cagtcagcta ttttatggca cacttttttt gactgatgac atctcctttg    780
ctatacctca atttttggaa tttagagaag aaatcagtag ttttgcaatg ttaattattt     840
agatattcaa tttcgcagat ttttaaactt tattttcata atttctgctt aatgtttaaa     900
attgaagagc cttttcatgt attaaataat gaacacaaat tatataatta aaataattgg     960
agatgttgaa aatcattttc ccttcttaaa cagaaataaa tatttggaat gaaggggaat    1020
gtactagaac accctttttg ccacgggtaa aaataacaga aatgtatggt ttgttttacc    1080
ttcatttctg tacaagtaaa gcttattagt ctaatgtttt gttcctttcc cacctcaccc    1140
ctacctcttt tgttttgttt tgttttttgcc ctttatgtac tacattctta ttttctaact   1200
tttaaacact gtattggagg tttttttttt taatttacag atcatattta ttttactatt    1260
```

-continued

```
tttgtagaaa attattaatt ttgattgtat ttttgtattt taaaagcttc ttcacttgtg    1320
ttccctaaat attcatattg ctgcccaaaa gtatgactgt ggaggaaaaa aaaatacttt    1380
aaaaatccac acttttgtt aagaaggaaa catttagcat ttatatattt gtgtatggaa     1440
aacacttgat attttatccc tgttgcatct ggctgcacag agcctctcct caaagatgct    1500
acaaaacttg aatataacac attttggaag gctgactaac ctcgattctg tgttgtgatg    1560
tgcaatactg tttctaatgt ttgtataaaa aaaaacagtg taaacctttt taatgcaaat    1620
ttattttttt cattgcatat tttgcagatt ttatccacag tgtcattttt tactgtcaga    1680
aaagataccc cttttgtcat tgcaactatt ttttaaatcc agaaatcttt gtaactgatg    1740
taaatgattg tagttatttt gggatagtgt tttggctaac aaaagggaga gactttttc     1800 atggcatatt tctattttgt ttttttgggt tttatttat tttaatagtt agtaaaatac      1860
ttgggaataa ttttgcata ttcttgttca ttaatattat tttgtatttt tatgtggaaa      1920
tatataattt tatgacacta attgctaaag tttatttat gttgaattat ttttggagct     1980
gaaatctttg taatattaaa gcaactagtt tctaattccc agtttctgta tagaatcgca    2040
caagtggttt atggagtgtt tggattgtaa ttataaatgg ttctttgata tgcaaattaa    2100 tatttcagt tgattttatt ttatattcct aatggggtgt taaagccgtt ttttatttt     2160 ttctaaataa aaagagaacc catgctttta tggacactag gtaaacacct tcagcttaaa    2220
tttttcgtta aatattttag tttattttat tgttatcttc caggtgtcta aatctccagt    2280
ctgtctgttg tactggtaat ttaactctgt aatggaatag tttgctgcca actatttata    2340
ttaagtaatt tttaaatatt tgtaatattg ttgactgact aataaactat taagttattg    2400
gaangaaaaa canaaaaaaa aanannaac                                      2429
```

<210> SEQ ID NO 4
<211> LENGTH: 944
<212> TYPE: DNA
<213> ORGANISM: Homo sapiens
<220> FEATURE:
<221> NAME/KEY:
<223> OTHER INFORMATION: 2009569
<300> PUBLICATION INFORMATION:

<400> SEQUENCE: 4

```
gcttgaaggc gggaaaatac ggaatggagc gacagggagt ggacgtgccc catgtgaaat     60
gcaaagacca ggaaccgcag cccttggggg agagcaagga gcatccgcgg tgggaagaga    120
actgcgagga ggaagctggt ggagggccag ctagtgccag ttgccagctg acggtcctgg    180
aagggaagtc gggactctac ttctcctctc tggactcaag cattgacatc ctgcagaaga    240
gagcccagga gctgatcgaa acatcaaca agagccggca aaaggaccat gcactcatga    300
ccaacttcag gaacagcctg aagaccaagg tttcggatct gacagagaaa ttagaggaga    360
ggatctatca gatttataat gaccacaaca agatcatcca ggaaaagctc caagagttca    420
cccagaaaat ggcaaagatc agccatttgg agacagagct caaacaagtc tgccacagcg    480
tggagactgt gtacaaagac ctgtgtctcc agcctgagca gagcctaaga ctcagatggg    540
ggccagacca ctctaggga aagtccccac cacgtcccgg caactcacag cccccagacg     600
tgttcgtttc ttctgtggct gaaactactt ctcaggccac tgcttcagaa gtacagacca    660
acagagatgg tgaatgctga cagctgccgg gagactcacg ccttagtgac agtctccagg    720
agaagactgt gaggccacca tttgggccac actgagaaat tgttttttcat ggttctataa    780 tgcatcttgg cagaaaaaaa caaaaaccca agctccttg tgctgaactc ccaaaatgta     840
```

```
gcaagtccag ccctctccat aggcccaggc ttcgtgctcc ccaccccttgg caagttctcc    900 ccaccccag ccccacagtt tattaaatgt ttgattttca aaaa                      944
```

<210> SEQ ID NO 5
<211> LENGTH: 404
<212> TYPE: DNA
<213> ORGANISM: Homo sapiens
<220> FEATURE:
<221> NAME/KEY:
<223> OTHER INFORMATION: 1642580
<300> PUBLICATION INFORMATION:

<400> SEQUENCE: 5

```
ctcaagaccc agcagtggga cagccagaca gacggcacga tggcactgag ctcccagatc    60
tgggccgctt gcctcctgct cctcctcctc ctcgccagcc tgaccagtgg ctctgttttc   120
ccacaacaga cgggacaact tgcagagctg caaccccagg acagagctgg agccagggcc   180
agctggatgc ccatgttcca gaggcgaagg aggcgagaca cccacttccc catctgcatt   240
ttctgctgcg gctgctgtca tcgatcaaag tgtgggatgt gctgcaagac gtagaaccta   300
cctgccctgc ccccgtcccc tcccttcctt atttattcct gctgccccag aacataggtc   360
ttggaataaa atggctggtt cttttgtttt ccaaaaaaaa aaaa                    404
```

<210> SEQ ID NO 6
<211> LENGTH: 587
<212> TYPE: PRT
<213> ORGANISM: Homo sapiens
<220> FEATURE:
<221> NAME/KEY:
<223> OTHER INFORMATION: 1851405
<300> PUBLICATION INFORMATION:

<400> SEQUENCE: 6

```
Met Ser Asn Val Met Gly Asn Thr Thr Trp Thr Thr Ser Gly Leu
 1               5                  10                  15

Lys Ser Gln Gly Arg Leu Ser Val Gly Ser Asn Arg Asp Arg Glu
                20                  25                  30

Ile Ser Met Ser Val Gly Leu Gly Arg Ser Gln Leu Asp Ser Lys
                35                  40                  45

Gly Gly Val Val Gly Gly Thr Ile Asp Val Asn Ala Leu Glu Met
                50                  55                  60

Val Ala His Ile Ser Glu His Pro Asn Gln Gln Pro Ser His Lys
                65                  70                  75

Ile Gln Ile Thr Met Gly Ser Thr Glu Ala Arg Val Asp Tyr Met
                80                  85                  90

Gly Ser Ser Ile Leu Met Gly Ile Phe Ser Asn Ala Asp Leu Lys
                95                 100                 105

Leu Gln Asp Glu Trp Lys Val Asn Leu Tyr Asn Thr Leu Asp Ser
               110                 115                 120

Ser Ile Thr Asp Lys Ser Glu Ile Phe Val His Gly Asp Leu Lys
               125                 130                 135

Trp Asp Ile Phe Gln Val Met Ile Ser Arg Ser Thr Thr Pro Asp
               140                 145                 150

Leu Ile Lys Ile Gly Met Lys Leu Gln Glu Phe Thr Gln Gln
               155                 160                 165

Phe Asp Thr Ser Lys Arg Ala Leu Ser Thr Trp Gly Pro Val Pro
               170                 175                 180
```

-continued

```
Tyr Leu Pro Pro Lys Thr Met Thr Ser Asn Leu Glu Lys Ser Ser
            185                 190                 195

Gln Glu Gln Leu Leu Asp Ala Ala His His Arg His Trp Pro Gly
            200                 205                 210

Val Leu Lys Val Val Ser Gly Cys His Ile Ser Leu Phe Gln Ile
            215                 220                 225

Pro Leu Pro Glu Asp Gly Met Gln Phe Gly Gly Ser Met Ser Leu
            230                 235                 240

His Gly Asn His Met Thr Leu Ala Cys Phe His Gly Pro Asn Phe
            245                 250                 255

Arg Ser Lys Ser Trp Ala Leu Phe His Leu Glu Pro Asn Ile
            260                 265                 270

Ala Phe Trp Thr Glu Ala Gln Lys Ile Trp Glu Asp Gly Ser Ser
            275                 280                 285

Asp His Ser Thr Tyr Ile Val Gln Thr Leu Asp Phe His Leu Gly
            290                 295                 300

His Asn Thr Met Val Thr Lys Pro Cys Gly Ala Leu Glu Ser Pro
            305                 310                 315

Met Ala Thr Ile Thr Lys Ile Thr Arg Arg His Glu Asn Pro
            320                 325                 330

Pro His Gly Val Ala Ser Val Lys Glu Trp Phe Asn Tyr Val Thr
            335                 340                 345

Ala Thr Arg Asn Glu Glu Leu Asn Leu Leu Arg Asn Val Asp Ala
            350                 355                 360

Asn Asn Thr Glu Asn Ser Thr Thr Val Lys Asn Ser Ser Leu Leu
            365                 370                 375

Ser Gly Phe Arg Gly Gly Ser Ser Tyr Asn His Glu Thr Glu Thr
            380                 385                 390

Ile Phe Ala Leu Pro Arg Met Gln Leu Asp Phe Lys Ser Ile His
            395                 400                 405

Val Gln Glu Pro Gln Glu Pro Ser Leu Gln Asp Ala Ser Leu Lys
            410                 415                 420

Pro Lys Val Glu Cys Ser Val Val Thr Glu Phe Thr Asp His Ile
            425                 430                 435

Cys Val Thr Met Asp Ala Glu Leu Ile Met Phe Leu His Asp Leu
            440                 445                 450

Val Ser Ala Tyr Leu Lys Glu Lys Glu Lys Ala Ile Phe Pro Pro
            455                 460                 465

Arg Ile Leu Ser Thr Arg Pro Gly Gln Lys Ser Pro Ile Ile Ile
            470                 475                 480

His Asp Asp Asn Ser Ser Asp Lys Asp Arg Glu Asp Ser Ile Thr
            485                 490                 495

Tyr Thr Thr Val Asp Trp Arg Asp Phe Met Cys Asn Thr Trp His
            500                 505                 510

Leu Glu Pro Thr Leu Arg Leu Ile Ser Trp Thr Gly Arg Lys Ile
            515                 520                 525

Asp Pro Val Gly Val Asp Tyr Ile Leu Gln Lys Leu Gly Phe His
            530                 535                 540

His Ala Arg Thr Thr Ile Pro Lys Trp Leu Gln Arg Gly Val Met
            545                 550                 555

Asp Pro Leu Asp Lys Val Leu Ser Val Leu Ile Lys Lys Leu Gly
            560                 565                 570

Thr Ala Leu Gln Asp Glu Lys Glu Lys Lys Gly Lys Asp Lys Glu
```

575                 580                 585

Glu His

<210> SEQ ID NO 7
<211> LENGTH: 218
<212> TYPE: PRT
<213> ORGANISM: Homo sapiens
<220> FEATURE:
<221> NAME/KEY:
<223> OTHER INFORMATION: 2009569
<300> PUBLICATION INFORMATION:

<400> SEQUENCE: 7

Met Glu Arg Gln Gly Val Asp Val Pro His Val Lys Cys Lys Asp
 1               5                  10                  15

Gln Glu Pro Gln Pro Leu Gly Glu Ser Lys Glu His Pro Arg Trp
                20                  25                  30

Glu Glu Asn Cys Glu Glu Ala Gly Gly Pro Ala Ser Ala
                35                  40                  45

Ser Cys Gln Leu Thr Val Leu Glu Gly Lys Ser Gly Leu Tyr Phe
                50                  55                  60

Ser Ser Leu Asp Ser Ser Ile Asp Ile Leu Gln Lys Arg Ala Gln
                65                  70                  75

Glu Leu Ile Glu Asn Ile Asn Lys Ser Arg Gln Lys Asp His Ala
                80                  85                  90

Leu Met Thr Asn Phe Arg Asn Ser Leu Lys Thr Lys Val Ser Asp
                95                 100                 105

Leu Thr Glu Lys Leu Glu Glu Arg Ile Tyr Gln Ile Tyr Asn Asp
               110                 115                 120

His Asn Lys Ile Ile Gln Glu Lys Leu Gln Glu Phe Thr Gln Lys
               125                 130                 135

Met Ala Lys Ile Ser His Leu Glu Thr Glu Leu Lys Gln Val Cys
               140                 145                 150

His Ser Val Glu Thr Val Tyr Lys Asp Leu Cys Leu Gln Pro Glu
               155                 160                 165

Gln Ser Leu Arg Leu Arg Trp Gly Pro Asp His Ser Arg Gly Lys
               170                 175                 180

Ser Pro Pro Arg Pro Gly Asn Ser Gln Pro Pro Asp Val Phe Val
               185                 190                 195

Ser Ser Val Ala Glu Thr Thr Ser Gln Ala Thr Ala Ser Glu Val
               200                 205                 210

Gln Thr Asn Arg Asp Gly Glu Cys
               215

<210> SEQ ID NO 8
<211> LENGTH: 84
<212> TYPE: PRT
<213> ORGANISM: Homo sapiens
<220> FEATURE:
<221> NAME/KEY:
<223> OTHER INFORMATION: 1642580
<300> PUBLICATION INFORMATION:

<400> SEQUENCE: 8

Met Ala Leu Ser Ser Gln Ile Trp Ala Ala Cys Leu Leu Leu Leu
 1               5                  10                  15

Leu Leu Leu Ala Ser Leu Thr Ser Gly Ser Val Phe Pro Gln Gln
                20                  25                  30

```
Thr Gly Gln Leu Ala Glu Leu Gln Pro Gln Asp Arg Ala Gly Ala
            35                  40                  45

Arg Ala Ser Trp Met Pro Met Phe Gln Arg Arg Arg Arg Asp
        50                  55                  60

Thr His Phe Pro Ile Cys Ile Phe Cys Cys Gly Cys Cys His Arg
            65                  70                  75

Ser Lys Cys Gly Met Cys Cys Lys Thr
            80
```

<210> SEQ ID NO 9
<211> LENGTH: 644
<212> TYPE: DNA
<213> ORGANISM: Rattus norvegicus
<220> FEATURE:
<221> NAME/KEY: unsure
<222> LOCATION: 44
<223> OTHER INFORMATION: a or g or c or t, unknown, or other
<220> FEATURE:
<221> NAME/KEY:
<223> OTHER INFORMATION: 700062690
<300> PUBLICATION INFORMATION:

<400> SEQUENCE: 9

```
ttgatctagt gtcagcatat ctgaaagaaa aggaaaaggc catntttcca cctcggattt      60
tatccactcg accaggacaa aagtgtccag ttattataca ggatgacaat tcctctgaca    120
gagacagaga agacggcatc acttacacca ctgtggactg gcgagacttt atgtgtaaca    180
catggcatct ggagcctact cttagattaa tttcttggac tggaagaaag attgatccag    240
taggtgttga ttacattctt caaaaattgg gctttcacca tgccaggact actattccca    300
aatggcttca gagaggagtg atggacccac tggataaggt gctatccgtt ctcatcaaaa    360
aactcgggac tgccctgcag gatgagaagg agaagaaagg aaaagacaaa gaagaacact    420
agaatagtaa ctccatctgt gaagtacctg actctgtccg ttaagttctg gcactgcaat    480
tttttcagca taactttaaa tggtacttca aaataattct aattttgtgg ccattattga    540
aacagtttgt aagttaatct gtttattcta gctctaccat tctgcataca gtaaagtatt    600
gcatgaaatg tacattttgt agaaaaacta aattaaaaga tata                     644
```

<210> SEQ ID NO 10
<211> LENGTH: 449
<212> TYPE: DNA
<213> ORGANISM: Rattus norvegicus
<220> FEATURE:
<221> NAME/KEY:
<223> OTHER INFORMATION: 700140450
<300> PUBLICATION INFORMATION:

<400> SEQUENCE: 10

```
gttcctaaag agaagtcact caacatggat gctatgaaaa gagggactgt ccctggagat      60
actcttttca gaccaatatc cacaggtccg caggtggctg gccccttca tcgttgcctg     120
ctccctctac ttcctcctct ggattcctga ggaccagcca tcttgggtca gtgcccggt     180
caagtgccag cccattctct gcctggtttt gttcctgtgg gctgtggctc ctggtgggag    240
ctacacctgg ctcctgcagg gagctcttac atgttctgct gttggagatg cctgcctcat    300
ctggcctgaa gctttctttt atggcatggc agtcttctct gttgcccact tactctacct    360
ctgggctttt ggcctgtctc cactgcagcc tggattgctg ctgtgcacca ccttggcctc    420
tctgacatac tacagcttcc tcctgctac                                      449
```

<210> SEQ ID NO 11
<211> LENGTH: 259
<212> TYPE: DNA
<213> ORGANISM: Rattus norvegicus
<220> FEATURE:
<221> NAME/KEY:
<223> OTHER INFORMATION: 700367683
<300> PUBLICATION INFORMATION:

<400> SEQUENCE: 11

```
gccgtttttt attttttct aaataaaaag agaacccatg cttttatgga cactaggtaa      60
aacgccttca gcttaaaatt tttgttaaat aatttagttt attttattgt tatcttccag     120
gtgtctaaat ctccagtctg tctgttgtac tggtaattta actctgtaat ggaatagttt    180
gctgccaact atttatatta agtcatttt aaatatttgt aatattgttg actgactaat     240
aaactattaa gttattggc                                                  259
```

<210> SEQ ID NO 12
<211> LENGTH: 261
<212> TYPE: DNA
<213> ORGANISM: Rattus norvegicus
<220> FEATURE:
<221> NAME/KEY:
<223> OTHER INFORMATION: 701316810
<300> PUBLICATION INFORMATION:

<400> SEQUENCE: 12

```
gtctcagatc tgacagaaaa gttggaggaa aggatgtacc aggtatacag ccaccacagc      60
aaaatcattc aggaaagact acaagaattt acccagaaga tggcaaagat cagtcatctg    120
gaaatggagc tcaaacaagt ttgccaaact gtggaaacta tgtacaagga cctatgtgtc    180
cagtctgagg taagaatttg ggggtgtatc ctgtgagaaa ggagaccgga agtaaaaca    240
tgaatgggaa ctttgacttc t                                                261
```

<210> SEQ ID NO 13
<211> LENGTH: 406
<212> TYPE: DNA
<213> ORGANISM: Rattus norvegicus
<220> FEATURE:
<221> NAME/KEY:
<223> OTHER INFORMATION: 700139271
<300> PUBLICATION INFORMATION:

<400> SEQUENCE: 13

```
tcaagtcctt ggactacact gcaggacaga aggcaagatg gcactaagca ctcggatcca      60
ggctgcctgt ctcctgcttc tcctcctggc cagcctgagc agcggtgcct atctccggca    120
acagacgaga cagactacgg ctctgcagcc ttggcatggg gcagaaagca agactgatga    180
cagtgcgctg ctgatgctga agcgaaggaa gcgagacacc aacttcccca tatgcctctt    240
ctgctgtaaa tgctgtaaga attcctcctg tggtctctgt tgcataacat agagagccaa    300
gagccttgtc ctgacctctc aacacactgc ctcccctccg ccccattatt tattcctgtc    360
ctaccccagc aatgaccttg aaataaaaat gatgatttta ttttca                    406
```

<210> SEQ ID NO 14
<211> LENGTH: 84
<212> TYPE: PRT
<213> ORGANISM: Rattus norvegicus
<220> FEATURE:
<221> NAME/KEY:
<223> OTHER INFORMATION: 700139271
<300> PUBLICATION INFORMATION:

-continued

```
<400> SEQUENCE: 14

Met Ala Leu Ser Thr Arg Ile Gln Ala Ala Cys Leu Leu Leu Leu
 1               5                  10                  15

Leu Leu Ala Ser Leu Ser Ser Gly Ala Tyr Leu Arg Gln Gln Thr
                20                  25                  30

Arg Gln Thr Thr Ala Leu Gln Pro Trp His Gly Ala Glu Ser Lys
                35                  40                  45

Thr Asp Asp Ser Ala Leu Leu Met Leu Lys Arg Arg Lys Arg Asp
                50                  55                  60

Thr Asn Phe Pro Ile Cys Leu Phe Cys Cys Lys Cys Cys Lys Asn
                65                  70                  75

Ser Ser Cys Gly Leu Cys Cys Ile Thr
                80
```